(12) United States Patent
Romrell et al.

(10) Patent No.: US 10,264,997 B1
(45) Date of Patent: Apr. 23, 2019

(54) SYSTEMS AND METHODS FOR SELECTING ACCELEROMETER DATA TO STORE ON COMPUTER-READABLE MEDIA

(71) Applicant: CAPSULE TECHNOLOGIES, INC., San Diego, CA (US)

(72) Inventors: Gregory R. Romrell, Sandy, UT (US); Catherine Basul dela Cuadra, Minglanilla (PH); Vanilyn Jereza Gomez, Cebu (PH); Mary Ann Antepuesto Lim, Cebu (PH)

(73) Assignee: CAPSULE TECHNOLOGIES, INC., San Diego, CA (US)

( * ) Notice: Subject to any disclaimer, the term of this patent is extended or adjusted under 35 U.S.C. 154(b) by 245 days.

(21) Appl. No.: 15/099,294

(22) Filed: Apr. 14, 2016

Related U.S. Application Data

(60) Provisional application No. 62/307,167, filed on Mar. 11, 2016, provisional application No. 62/153,288, filed on Apr. 27, 2015.

(51) Int. Cl.
*A61B 5/00* (2006.01)
*A61B 5/11* (2006.01)

(52) U.S. Cl.
CPC ............ *A61B 5/1118* (2013.01); *A61B 5/112* (2013.01); *A61B 5/6823* (2013.01); *A61B 5/6824* (2013.01); *A61B 5/6831* (2013.01); *A61B 5/7278* (2013.01); *A61B 2562/0219* (2013.01)

(58) Field of Classification Search
None
See application file for complete search history.

(56) References Cited

U.S. PATENT DOCUMENTS

| 8,600,928 | B2* | 12/2013 | Landers | G06F 17/40 706/61 |
| 9,191,442 | B2 | 11/2015 | Kuntagod et al. | |
| 2015/0019135 | A1* | 1/2015 | Kacyvenski | A61B 5/0488 702/19 |
| 2016/0058314 | A1* | 3/2016 | Chu | A61B 5/02438 600/508 |

OTHER PUBLICATIONS

Del Din, Silvia; Godfrey, Alan; and Rochester, Lynn. "Validation of an accelerometer to quantify a comprehensive battery of gait characteristics in healthy older adults and Parkinson's disease: toward clinical and at home use." IEEE Journal of Biomedical and Health Informatics. Apr. 2015.

(Continued)

*Primary Examiner* — Reema Patel
*Assistant Examiner* — Steven M Christopher

(57) ABSTRACT

Systems and methods select accelerometer data to store on computer-readable media. Systems may comprise an accelerometer, a processor, and a computer-readable medium storing instructions executed by the processor. Accelerometer data from a critical time period are stored on a computer readable medium if an activity ratio for the critical time period exceeds an activity threshold. The numerator of the activity ratio comprises a count of data windows in the critical time period that satisfy one or more count criteria and the denominator comprises the total number of data windows in the critical time period.

22 Claims, 20 Drawing Sheets

(56) References Cited

OTHER PUBLICATIONS

Moe-Nilssen, Rolf; and Helbostad, Jorunn. "Estimation of gait cycle characteristics by trunk accelerometry." Journal of Biomechanics 37.1: pp. 121-126 (2004).

Sant' Ana, Anita; Ourique De Morais, Wagner; and Wickstrom, Nicholas. "Gait Unsteadiness Analysis from Motion Primitives." Gerontechnology: international journal on the fundamental aspects of technology to serve the ageing society 7.2 (2008): 204.

Sant' Ana, Anita; and Wickstrom, Nicholas. "Developing a Motion Language: Gait Analysis from Accelerometer Sensors." Pervasive Computing Technologies for Healthcare, 2009. Pervasive Health 2009. 3rd International Conference on. IEEE, 2009.

Satkunskeine, Danguole; Grigas, Vytautus; Eidukynas, V.; and Domeika, A. "Acceleration based ?Naluation of the human walking and running parameters." Journal of Vibroengineering, 11.3: pp. 506-510 (2009).

Sayeed, Taufique; Sama, Albert; Catala, Andreu; and Cabestany, Joan. "Comparison and adaptation of step length and gait speed estimators from single belt worn accelerometer positioned on lateral side of the body." 2013 IEEE 8th International Symposium on Intelligent Signal Processing (WISP), 2013.

Tura, Andrea; Raggi, Michele; Rocchi, Laura; Cutti, Andrea; and Chiari, Lorenzo.. "Gait symmetry and regularity in transfemoral amputees assessed by trunk accelerations." Journal of Neuroengineering and Rehabilitation 7.1 (2010): 1.

\* cited by examiner

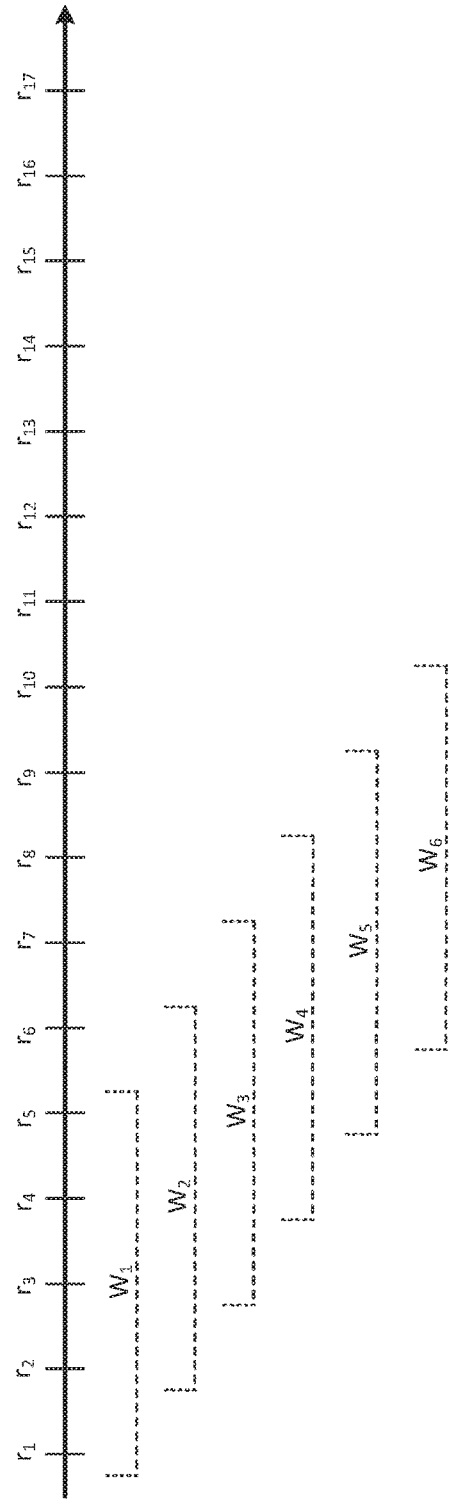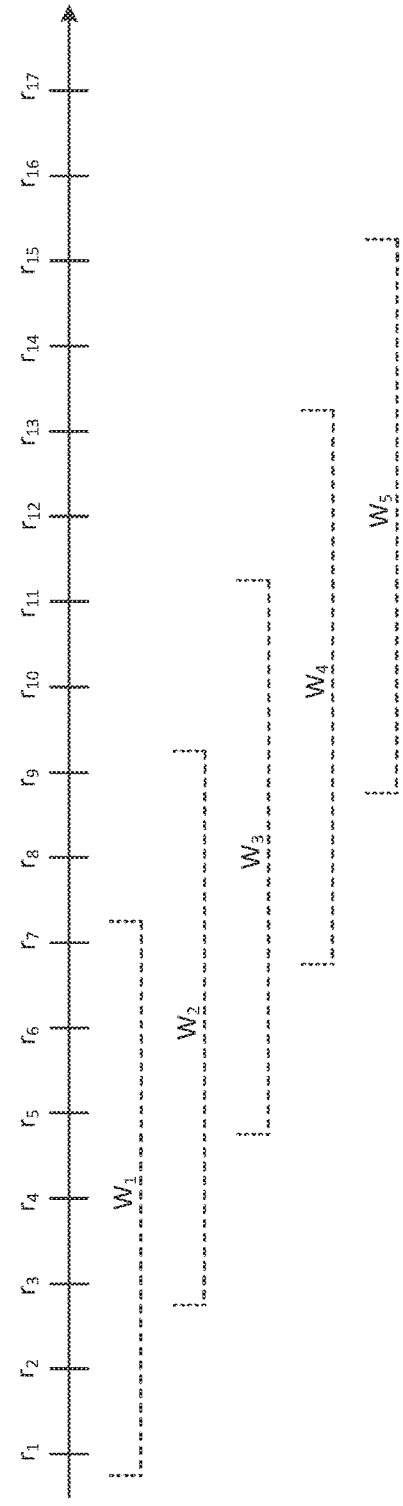

Time Periods

Threshold-Determined Segments

Local Minima and Maxima

US 10,264,997 B1

SYSTEMS AND METHODS FOR SELECTING ACCELEROMETER DATA TO STORE ON COMPUTER-READABLE MEDIA

This application claims the benefit of U.S. Provisional Application No. 62/153,288, filed Apr. 27, 2015 and of U.S. Provisional Application No. 62/307,167 filed, Mar. 11, 2016, the entire contents of which are hereby incorporated by reference.

FIELD OF THE INVENTION

Embodiments relate to processor-implemented selection of accelerometer data to be stored on computer-readable media.

BACKGROUND

Accelerometers may be used in activity trackers which monitor the physical activity of the users who carry them. Activity may be reported to the user in a variety of units including steps taken, distance traveled, or calories burned. The units of activity may be derived from the accelerometer data using various computational algorithms. The information from activity trackers can be useful in understanding the activity patterns of users and may motivate them to higher activity levels.

Accelerometers generate readings representing acceleration. These readings can accumulate into large quantities of data. Data storage capacity on activity trackers is limited. Furthermore, some time periods generate more useful data than others. For example, periods of activity may contain more useful information than periods of inactivity. Selecting and storing data only from more pertinent time periods may allow data storage to be used more efficiently than indiscriminately storing all data. For some applications, it may be advantageous to store data from a time period when there is a high probability that the user is walking, running, or otherwise taking steps. However, step activity may be difficult to distinguish from other types of motion.

BRIEF DESCRIPTION

Systems and methods select accelerometer data to store on computer readable media. Systems may comprise an accelerometer, a processor, and a computer-readable medium storing instructions executed by the processor. The instructions control the processor to group accelerometer readings into data windows and count those windows satisfying one or more count criteria. In some embodiments, windows in which at least one reading exceeds a count threshold are counted. Some embodiments determine a window value for each window. The window value may comprise a measure of central tendency of the readings in each data window. Embodiments may then identify local maxima in the window values and count those local maxima that exceed a count threshold. The processor may then determine an activity ratio in which the numerator comprises the number of counted windows in a critical time period and the denominator comprises the total number of windows in the critical time period. If the activity ratio exceeds an activity threshold, data from the critical time period may be stored on the computer readable medium.

BRIEF DESCRIPTION OF THE DRAWINGS

FIG. 4 presents a time line illustrating a sliding data window comprising five readings per window and advancing one reading per cycle, according to certain embodiments of the present disclosure.

FIG. 5 presents a time line illustrating a sliding data window comprising seven readings per window and advancing two readings per cycle, according to certain embodiments of the present disclosure.

DETAILED DESCRIPTION

Figure 1:
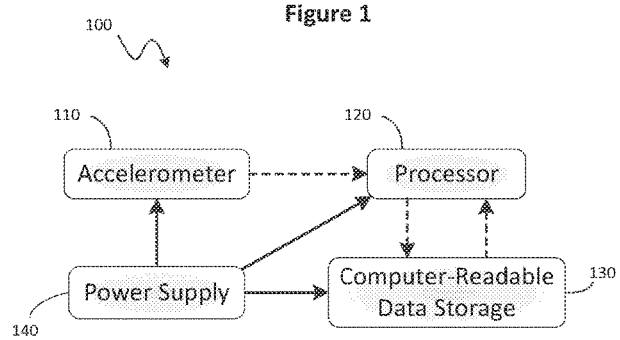
FIG. 1 presents a diagram illustrating a system for selecting accelerometer data to store on a computer-readable medium, according to certain embodiments of the present disclosure.

Embodiments include systems and methods for selecting portions of accelerometer data to store on computer-readable media. The selection is based on characteristics of the readings generated by the accelerometer during a critical time period.

Systems

Systems comprise an accelerometer generating readings, each of which represent an amount of acceleration. Plotted over time, the readings may be viewed as an acceleration signal. A reading may, optionally, include the direction or angle of acceleration. A reading may be referred to as a data point. Data may refer to multiple readings or values derived from readings. An accelerometer may refer to any device that measures either linear or angular acceleration, though accelerometers measuring angular acceleration may be referred to as gyroscopes, gyrometers, or gyros. An accelerometer may refer to a device that measures acceleration in more than one direction. For example, triaxial accelerometers measure acceleration on three axes that may be at least approximately orthogonal to one another. In addition to linear and angular acceleration, some accelerometers also contain a magnetometer that can orient accelerations relative to a magnetic field such as that of Earth. Devices containing a tri-axial accelerometer measuring linear acceleration along three orthogonal axes, angular acceleration around three orthogonal axes, and orientation relative to a magnetic field may be referred to as a 9-axis accelerometer or inertial measurement unit (IMU).

The accelerometer may be coupled to an individual whose activity is analyzed. In an exemplary embodiment, the accelerometer is coupled to the individual's wrist using a strap or similar means. In a second exemplary embodiment, the accelerometer may be coupled to the individual's torso by, for example, a belt around the hips or a lanyard around the neck.

The accelerometer may be communicatively coupled to a processor. A processor may include one or more processing units (i.e. processors communicatively coupled to one another). The processor may be communicatively coupled to and execute instructions stored on a computer readable data storage (CRDS) (also referred to herein as a non-transitory computer-readable medium or, simply, a computer readable medium). The instructions control the processor to select a subset of readings to store on the CDRS. Embodiments of the CRDS may include random access memory (RAM) and various types of non-volatile memory including, but not limited to, read-only memory (ROM), programmable read-only memory (PROM), erasable programmable read-only memory (EPROM), and/or electrically erasable programmable read-only memory (EEPROM). Embodiments of the CRDS may include magnetic storage (such as hard drives, floppy disks, and magnetic tape) and/or optical storage (such as CDs and DVDs).

Time measuring means may be used to estimate time periods used to select data for storage. Time periods may be measured using a variety of means. Because processors typically perform calculations on a regular time cycle, some embodiments may count processor cycles as a means for measuring time. If the accelerometer generates outputs at regular time intervals; embodiments may count the number of accelerometer outputs to measure the passage of time. Alternatively, a separate time-measuring device may be used to measure time periods. Examples of alternative time measuring devices include electric clocks such as quartz clocks, synchronous clocks, and radio-controlled clocks that are wirelessly synchronized with a time standard such as an atomic clock.

System components named above may consume energy from a power source. Power sources may include various types of batteries as well as devices that collect ambient energy such as sunlight (e.g. photo-voltaic cells), body heat, and body motion. An exemplary embodiment powers its components with a rechargeable lithium ion battery.

Components of the system may be communicatively coupled to other components. The processor, for instance, may receive information from the accelerometer, send information to the output device (if any), and both send and receive information from the CRDS. These communications may be made with or without physical connections such as wires. Any of the communications may be accomplished wirelessly using signal types including radio and infrared. Common wireless communication protocols include Bluetooth (IEEE 802.15), Wi-Fi (IEEE 802.11), cellular communication protocols, and infrared data association protocols. Embodiments using wireless communications may include components such as transmitters and receivers. Systems may also communicate with other devices or networks, for example a personal computer, smartphone or the Internet.

FIG. 1 illustrates a schematic diagram of a system (100) according to certain embodiments of the present disclosure. The system (100) includes an accelerometer (110) that sends readings to a processor (120). The dashed line connecting the two components indicates that they are communicatively coupled; information may be transferred from one to another, but does not necessarily require a physical connection. The processor (120) executes instructions stored on a computer-readable data storage (CRDS) (130). The processor (120) may store and retrieve data, such as accelerometer data, from the CRDS (130) and process the data to determine a subset of accelerometer readings or data to store on the CRDS (130). The components named above are powered by a power supply (140). While this diagram shows one power supply providing energy to each of the components, the system (100) may use multiple power sources. Any configuration of power sources may be used provided that each component receives power, either directly from a power supply or indirectly through other components.

Figure 2:
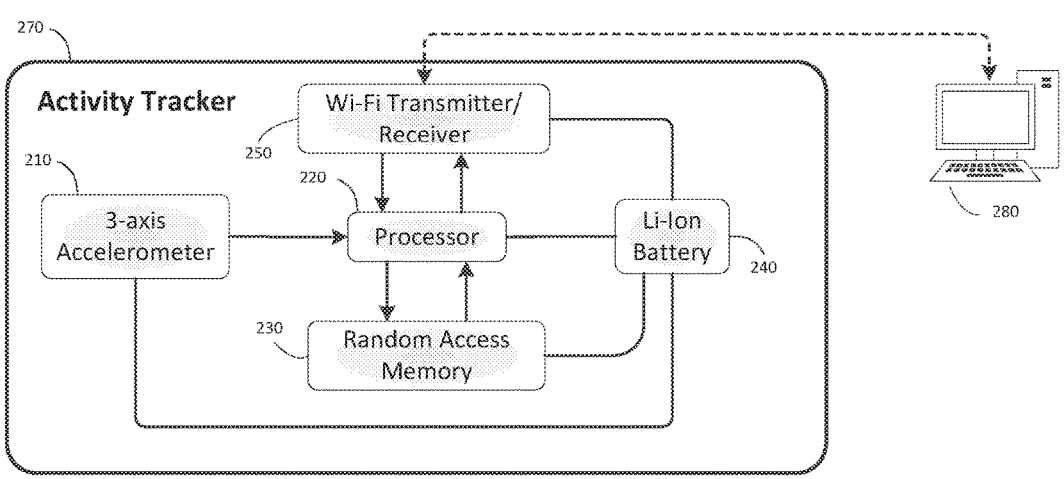
FIG. 2 presents a diagram illustrating a system for selecting accelerometer data to store on a computer-readable medium housed in a single device, according to certain embodiments of the present disclosure.

FIG. 2 illustrates a schematic diagram of a system (200) in a portable, self-contained activity tracker (270) according to certain embodiments of the present disclosure. The rectangle surrounding the components indicates that they are all housed in the same device. The activity tracker (270) includes a 3-axis accelerometer (210), a processor configured to function in the activity tracker (220), random access memory (RAM) (230), and a rechargeable lithium-ion (Li-Ion) battery (240). The processor (220) executes instructions stored on the RAM (230). From time to time, the activity tracker (270) may communicate with a second device (280) using radio signals. The activity tracker (270) contains a Wi-Fi transmitter-receiver (250) that exchanges data with the external device (280). The wireless communication may serve to communicate unprocessed readings or derived measures of physical activity to the external device (280) which may be communicatively coupled to networks such as the Internet.

Figure 3:
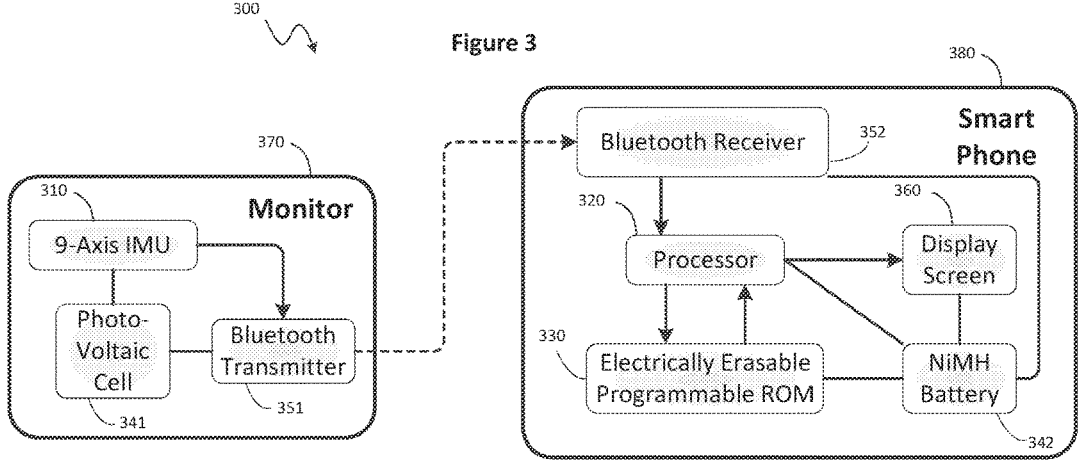
FIG. 3 presents a diagram illustrating a system for selecting accelerometer data to store on a computer-readable medium comprising a monitor device and separate smart phone, according to certain embodiments of the present disclosure.

FIG. 3 illustrates a schematic diagram of a system (300) in which a motion monitor (370) wirelessly transfers acceleration readings to an external device (380) for processing and possible storage, according to certain embodiments. In this embodiment, the external device is a smartphone (380). The motion monitor (370) contains a 9-axis accelerometer/IMU (310), a Bluetooth transmitter (351), and a photovoltaic cell (341) to power the other components. The Bluetooth transmitter (351) transmits the readings from the IMU (310) to a Bluetooth receiver (352) in the smartphone (380). The Bluetooth receiver (352) then relays the readings to the processor (320) which, in turn, processes the acceleration data according to instructions stored on an electrically erasable programmable read-only memory (EEPROM) (330) and determines which readings to store on the EEPROM (330). Components in the smartphone (380) are powered by a nickel metal-hydride (NIMH) battery (342). The smartphone (380) may, optionally, communicate raw or processed acceleration data to other external devices via cellular frequencies and data protocols.

Methods

Data Windows

Embodiments of processor-implemented methods analyze accelerometer readings in groups of readings called windows (also referred to as data windows). Windows may be described in terms of the number of readings in each window and the number of readings advanced from one window to the next. Windows may be overlapping, contiguous, or separated by one or more readings. The ideal number of readings in a window may depend on factors such as the rate at which the accelerometer generates acceleration readings and the type of activity the method is intended to detect. For example, if the method is designed to detect foot steps, the window may be the number of accelerometer readings generated during the time necessary to take a step. Exemplary embodiments use a window duration that is greater than or equal to 0.25 seconds and less than or equal to 1.5 seconds.

FIG. 4 presents a time line illustrating a sliding data window comprising five readings per window and advancing one reading per cycle, according to certain embodiments of the present disclosure. Accelerometer readings are represented with the variable r with a subscript indicating the sequential order of a reading ($r_1$ through $r_{17}$). The first window ($W_1$) consists of readings $r_1$ through $r_5$. The first reading of each window is the next subsequent reading after the first reading of the next previous window. Thus, the second window ($W_2$) consists of readings $r_2$ through $r_6$. Window $W_3$ consists of readings $r_3$ through $r_7$, and so forth. When successive windows overlap previous windows (include common readings), they may be referred to as sliding windows. Windows may slide at more than one reading per window.

FIG. 5 presents a time line illustrating a sliding data window comprising seven readings per window and advancing two readings per cycle, according to certain embodiments of the present disclosure. Accelerometer readings are represented with the variable r with a subscript indicating the sequential order of a reading ($r_1$ through $r_{17}$). The first window ($W_1$) consists of readings $r_1$ through $r_7$. The first reading of each window is the second subsequent reading after the first reading of the next previous window. Thus, the second window ($W_2$) consists of readings $r_3$ through $r_9$. Window $W_3$ consists of readings $r_5$ through $r_{11}$, and so forth. When successive windows overlap previous windows (include common readings), they may be referred to as sliding windows. However, successive windows may lack common readings.

Figure 6:
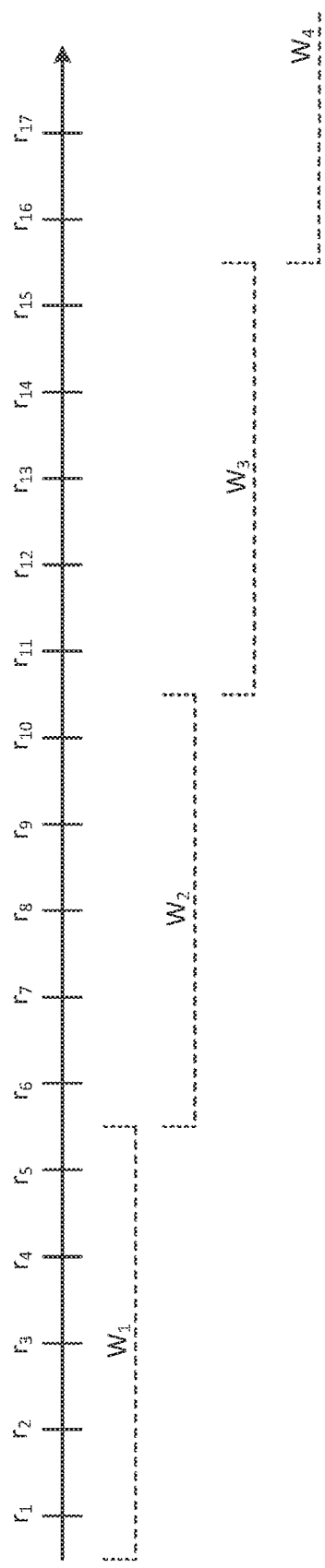
FIG. 6 presents a time line illustrating contiguous data windows comprising five readings per window and advancing five reading per cycle, according to certain embodiments of the present disclosure.

FIG. 6 presents a time line illustrating contiguous data windows comprising five readings per window and advancing five reading per cycle, according to certain embodiments of the present disclosure. Accelerometer readings are represented with the variable r with a subscript indicating the sequential order of a reading ($r_1$ through $r_{17}$). The first window ($W_1$) consists of readings $r_1$ through $r_5$. The first reading of each window is the fifth subsequent reading after the first reading of the next previous window. Thus, the second window ($W_2$) consists of readings $r_6$ through $r_{10}$. Window $W_3$ consists of readings $r_{11}$ through $r_{15}$, and so forth. Any embodiment in which the number of readings in each window is equal to the number of readings each window advances relative to the immediately previous window will have contiguous data windows. That is, the first reading in window $W_{X+1}$ is the reading immediately following the last reading in window $W_X$. The previous examples of data windows include each accelerometer reading in at least one window. This is not the case for all embodiments.

Figure 7:
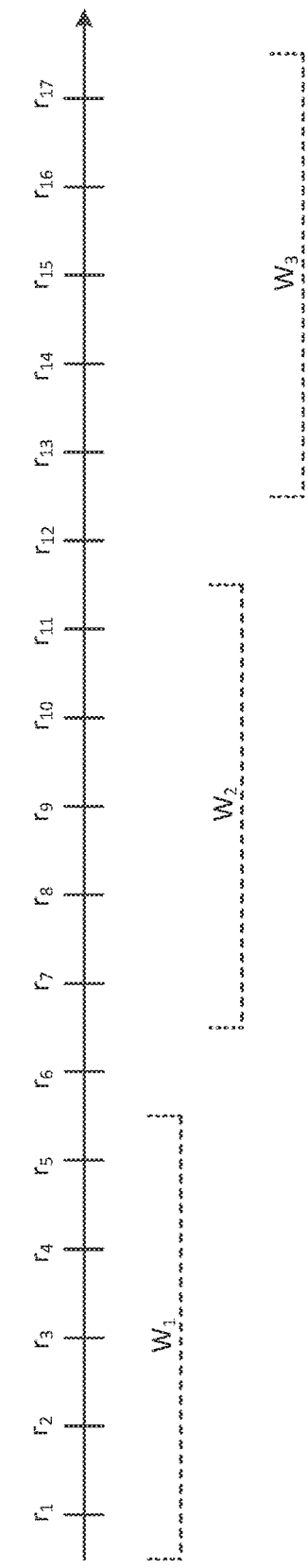
FIG. 7 presents a time line illustrating separated data windows comprising five readings per window and advancing six reading per cycle, according to certain embodiments of the present disclosure.

FIG. 7 presents a time line illustrating separated data windows comprising five readings per window and advancing six reading per cycle, according to certain embodiments of the present disclosure. Accelerometer readings are represented with the variable r with a subscript indicating the sequential order of a reading ($r_1$ through $r_{17}$). The first window ($W_1$) consists of readings $r_1$ through $r_5$. The first reading of each window is the sixth subsequent reading after the first reading of the next previous window. Thus, the second window ($W_2$) consists of readings $r_7$ through $r_{11}$. Window $W_3$ consists of readings $r_{13}$ through $r_{17}$, and so forth. Because the number of readings which each window advances relative to the immediately previous window is greater than the number of readings in each window, some readings are not included in any data window. In this embodiment, readings $r_6$ and $r_{12}$ are not included in any window.

Count Criteria and Activity Ratio

Embodiments may count those windows within a critical time period that satisfy one or more criteria. As with windows, critical time periods may be described in terms of duration and relative position (overlapping, contiguous, or separated by one or more readings). Considerations influencing the duration and relative position of critical time period may include processing resources, the activity type of interest, and the minimum duration of activity necessary to be meaningful. Exemplary embodiments may use a critical time period with a duration in the range of 10 seconds to five minutes.

The one or more criteria used to determine whether a window is counted may be referred to as count criteria. Some embodiments count windows whose readings satisfy a single count criterion. For example, some embodiments count windows in which at least one of the readings in the window exceeds a threshold (called a count threshold). Choice of the count threshold may depend on the activity of interest. Count thresholds may be low enough to detect the activity of interest but high enough to remove background noise from consideration. Exemplary embodiments use count thresholds greater than or equal to 0.2 g. and less than or equal to 0.8 g.

Some embodiments add one or more additional layers of processing, each layer with its own criterion, before generating a count. Some embodiments generate a window value for each window, determine which of the window values satisfies a first set of count criteria, and then count window values that satisfy a second set of count criteria. For example, some embodiments identify windows that qualify as peaks and then determine whether the peaks satisfy one or more count criteria. Examples of count criteria include thresholds. Count criteria may, for example, require values to exceed a threshold, be less than a threshold, or fall between two thresholds.

The number of windows in the critical time period satisfying the one or more count criteria, or a function of that number, may be used in the numerator of a fraction referred to as the activity ratio. The denominator of the activity ratio may be one of a variety of values that are indicative of the entire critical time period, or the results during the critical time period that did not satisfy the one or more count criteria. Examples of denominators include the number of windows in the critical time period, the number of windows in the critical time period that did not satisfy the one or more count criteria, or functions of either. For embodiments determining peaks in window values, examples of denominators may include the total number of peaks in the critical time period, the number of peaks that did not meet the one or more count criteria, or functions of either.

The activity ratio, or a function of it, may determine whether accelerometer data from a particular time period will be stored. For accelerometer data to be stored, the activity ratio (or a function of it) must meet one or more criteria (called ratio criteria). Ratio criteria are not necessarily the same as count criteria. Like the count criteria however, examples of ratio criteria may involve thresholds. Ratio criteria may require values to exceed a threshold, be less than a threshold, or fall between thresholds. Exemplary embodiments use a ratio threshold greater than or equal to 0.2 and less than or equal to 1.0.

If the activity ratio (or a function of it) meets the one or more ratio criteria, embodiments may store accelerometer data from a second time period on a computer-readable medium. The stored sample may consist of the readings generated during the critical time period, a subset of those readings, or readings from a time period that partially overlaps with the critical time period. Stored data may come from outside the critical period. The critical time period may have fixed beginning and end points, be a particular duration (length of time) without fixed beginning and end points, or be of variable duration depending on the accelerometer data or other conditions.

Figure 8:
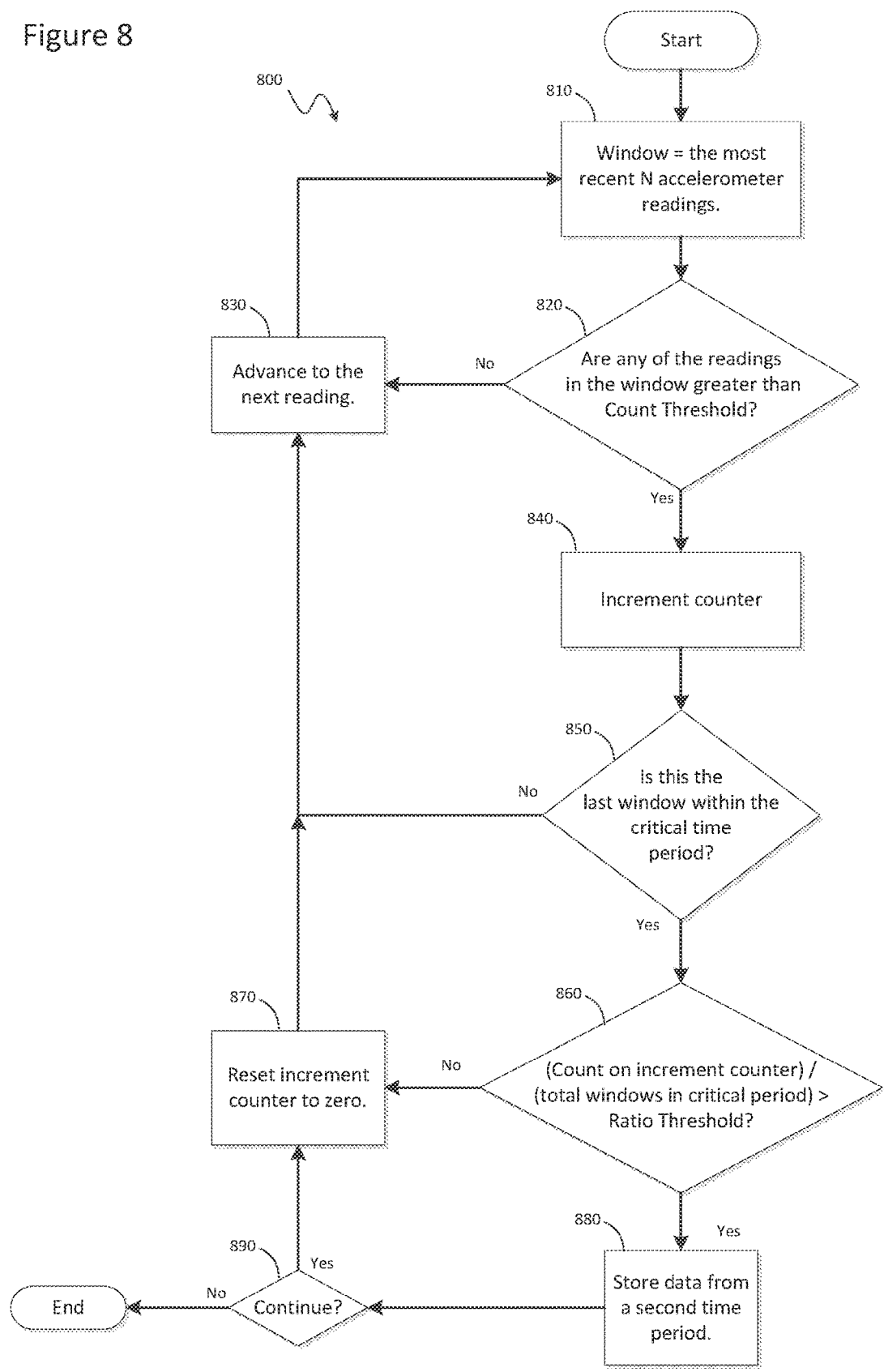
FIG. 8 presents a flowchart illustrating a method for selecting accelerometer data to store on a CRDS in which the windows overlap and the critical time periods are contiguous, according to certain embodiments of the present disclosure.

FIG. 8 presents a flowchart illustrating a processor-implemented method (800) for selecting accelerometer data to store on a CRDS in which the windows overlap and the critical time periods are contiguous, according to certain embodiments of the present disclosure. Each window is composed of the most recent N accelerometer readings (810). For some embodiments, N may be the number of readings that the accelerometer generates in 1.5 seconds. Because each window contains N readings, the windows analyzed for a particular critical time period may start N readings into the critical time period. (Other embodiments may consider N readings outside the critical time period.) Some embodiments may use a critical time period of one minute. The method (800) then determines whether any of the readings in the window exceed a count threshold (820). Some embodiments, for example, may use a count threshold of 0.625 g. if none of the accelerometer readings exceeds the count threshold, then the window advances to the next accelerometer reading (830) and processing considers the next window (810). If any of the accelerometer readings exceed the count threshold, an increment counter is increased by one unit (840). The method (800) then determines if the most recently analyzed window is the last window within a critical time period (850). If not, processing proceeds to the next reading (830). If the most recent window is the last in the critical time period, the method (800) then determines whether the activity ratio is greater than a activity threshold (860). Some embodiments, for example, use an activity threshold of 0.8. In this embodiment, the activity ratio is the count on the increment counter (the number of windows within the critical time period that exceed the count threshold) divided by the total number of windows in the critical time period (860). If the activity ratio is not greater than the activity threshold, the increment counter is reset to zero (870) and processing proceeds to the next accelerometer reading (830). If the activity ratio is greater than the activity threshold, the method stores accelerometer data from a second time period on a computer-readable medium (880). The method then determines whether to continue (890). If continuing, the increment counter is reset to zero (870), processing proceeds to the next window (830), and the process begins again (810).

Figure 9:
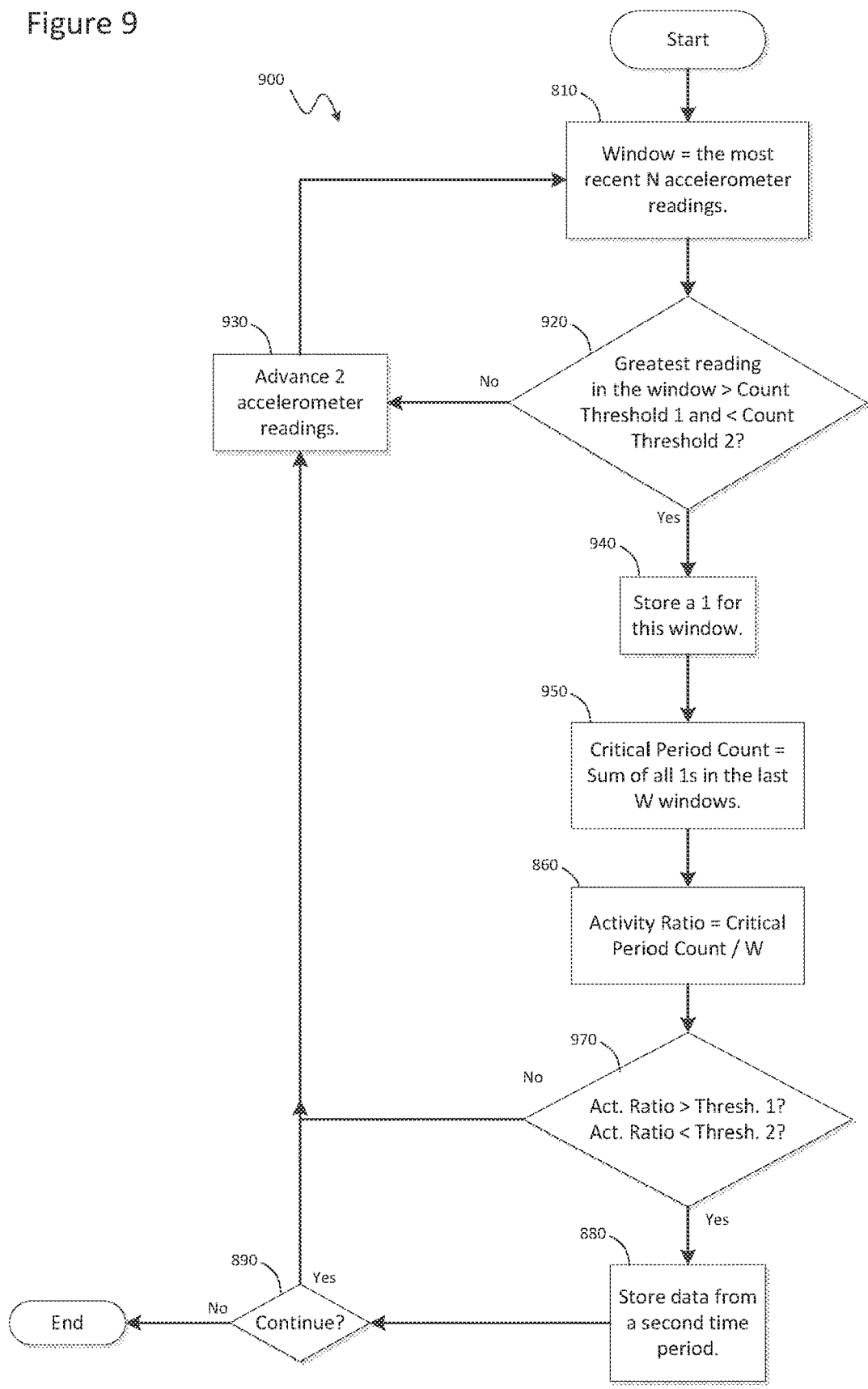
FIG. 9 presents a flowchart illustrating a method for selecting accelerometer data to store on a CRDS in which the windows overlap and the critical time periods overlap, according to certain embodiments of the present disclosure.

FIG. 9 presents a flowchart illustrating a processor-implemented method (900) for selecting accelerometer data to store on a CRDS in which the windows overlap and the critical time periods are contiguous, according to certain embodiments of the present disclosure. Each window is composed of the most recent N accelerometer readings (810). The method (900) then determines whether the greatest reading in the window exceeds a first count threshold and is less than a second count threshold (920). An upper threshold may be useful, for example, to screen out aberrant, high-acceleration events such as dropping the accelerometer on the ground. If the greatest reading in the window is not between the first and second thresholds, processing advances two readings (930) and considers a second window of the N most recent readings (810). If the greatest reading in the window is not between the first and second thresholds, the method stores a one (1) associated with information identifying the window's number (940). The critical time period is the current window and the last W windows and the count for any critical time period is the sum of all the ones associated with any of the last W windows (950). Thus, each critical time period overlaps the previous critical time period for any W greater than 1. The activity ratio is the count for the critical time period divided by the total number of windows (W) in the critical time period (860). The method (900) determines whether the activity ratio is greater than a first activity threshold and less than a second activity threshold (970). If not, the window advances two accelerometer readings (930) to the next window (810). If the activity ratio is greater than the first activity threshold and less than the second activity threshold, data from a second time period is recorded on a computer-readable medium (880). The method (900) then determines whether to continue (890) and, if not, advances the window two more readings (930).

Peaks and Amplitude

Some embodiments identify significant peaks and/or troughs in the signal of acceleration readings over time. There are a variety of ways to define a peak and to define which peaks are significant. Embodiments that identify peaks may then compare the number of peaks satisfying one or more criteria ("counted peaks") that occur during the critical time period to a reference value. As with other embodiments, the comparison may take the form of an activity ratio. For an activity ratio, the reference value may take the form of a denominator. Examples of denominators for the activity ratio include the total number of peaks within the critical time period or the number of peaks in the critical time period that were not counted. If the activity ratio or other comparison value meets one or more criteria, then accelerometer readings from a time period may be stored to a computer-readable medium. Criteria for the activity ratio may include, for example, thresholds including upper and/or lower thresholds. The recorded time period may be the same as the critical time period, a sub set of it, or partially overlap it.

Peak height and amplitude are two features that may be considered when analyzing accelerometer signals (acceleration readings over time). Peak height may refer to the highest reading of the instrument within a portion of data and amplitude may refer to the difference between the highest reading and the lowest reading within a portion of data. The lowest reading within a portion of data may be referred to as a trough height or a valley height. However, different definitions of peak height and amplitude specify different portions. The portion may be the data collected over a period of time. Alternatively, the portion may be determined by the instrument's readings, though this scenario could also be described as having a variable time period whose length is determined by the signal.

Some embodiments define peaks with time periods of a predetermined length. The length may be the same for all time periods, or time periods may be of different (but still predetermined) lengths. Alternatively, some embodiments define peaks according to variable time periods. Some of these embodiments use time periods that are determined by the data signal. For instance, one embodiment uses time periods that begin and end each time instrument readings exceed a threshold (after readings have been less than the threshold). Some embodiments define time periods as the time between a local maximum and an adjacent local minimum. Time periods may be contiguous, separated, or overlapping.

Figure 10:
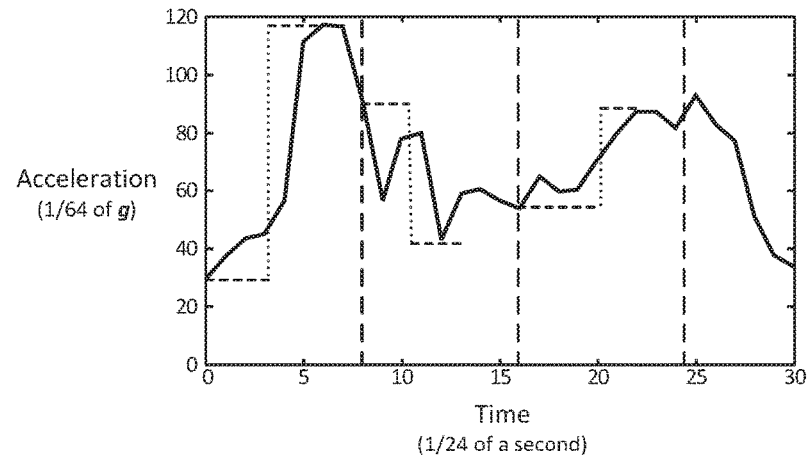
FIG. 10 illustrates definitions of peak height and amplitude based on fixed time periods.
Figure 11:
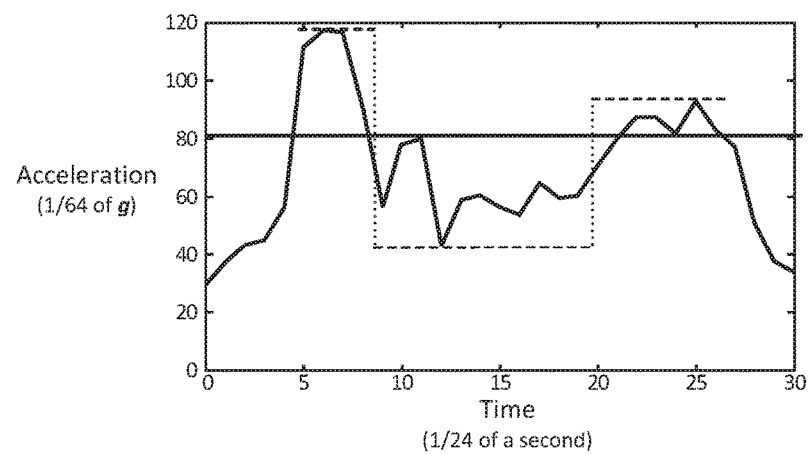
FIG. 11 illustrates definitions of peak height and amplitude based on time periods determined by thresholds.
Figure 12:
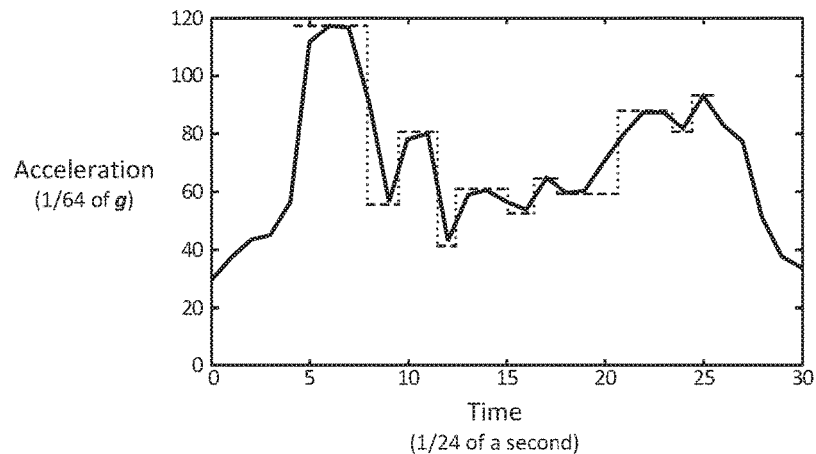
FIG. 12 illustrates definitions of peak height and amplitude based on local maxima and minima.

FIGS. 10 through 12 illustrate three ways to define peak height and amplitude. In each figure, the time scale on each x axis is in ¹⁄₂₄ths of a second and the units of acceleration on the y axis are ¹⁄₆₄th of g (g=free-fall acceleration in Earth's gravity). FIG. 10 illustrates peak height and amplitude defined relative to fixed time periods. In this embodiment, the time period is constant and set at ⅓ (⁸⁄₂₄) of a second. The boundaries between time periods are represented by the vertical dashed lines. The peak height and the trough height are the highest and lowest points within each time period and are represented by horizontal dashed lines. The length of the vertical dotted lines between the peak height and the trough height represents the amplitude for each time period.

FIG. 11 illustrates peak height and trough height as defined by a threshold. In this embodiment, the threshold has been set at ⁸⁰⁄₆₄ of g. The peak height is the highest point between two threshold crossings that is above the threshold and the trough height is the lowest point between two threshold crossings that is below the threshold. Peak height and trough height are represented by horizontal dashed lines and the amplitudes are represented by the lengths of the vertical dotted lines.

FIG. 12 illustrates the use of local maxima and minima as peak heights and trough heights, respectively. A reading immediately preceded by a lower reading and immediately followed by a lower reading is a local maximum. Conversely, a reading flanked on both sides by higher readings is a local minimum. In this embodiment, an amplitude is the difference in height between a peak height and a directly adjacent trough height. Again, peak heights and trough heights are represented by horizontal dashed lines and amplitudes are represented by the lengths of the vertical dotted lines.

One obstacle to using local maxima and minima is signal noise peaks and valleys in the data signal that are not caused by the physical activity of the user. There are a variety of techniques to reduce noise. In particular, some techniques eliminate local minima and maxima that are caused by noise. Down-sampling is one such technique. Down-sampling considers only data taken at fixed intervals. For instance, one embodiment of down-sampling considers only every third reading generated by an instrument. Another noise-reduction technique takes a measure of central tendency for each of a group of data points. Some embodiments use the average (mean) as the measure of central tendency. Taking the mean of each reading in a sliding window yields a moving average. When windows are discrete, the result is sometimes referred to as "box car averaging" or "box car filtering" to describe any function taken of discrete data windows.

Figure 13:
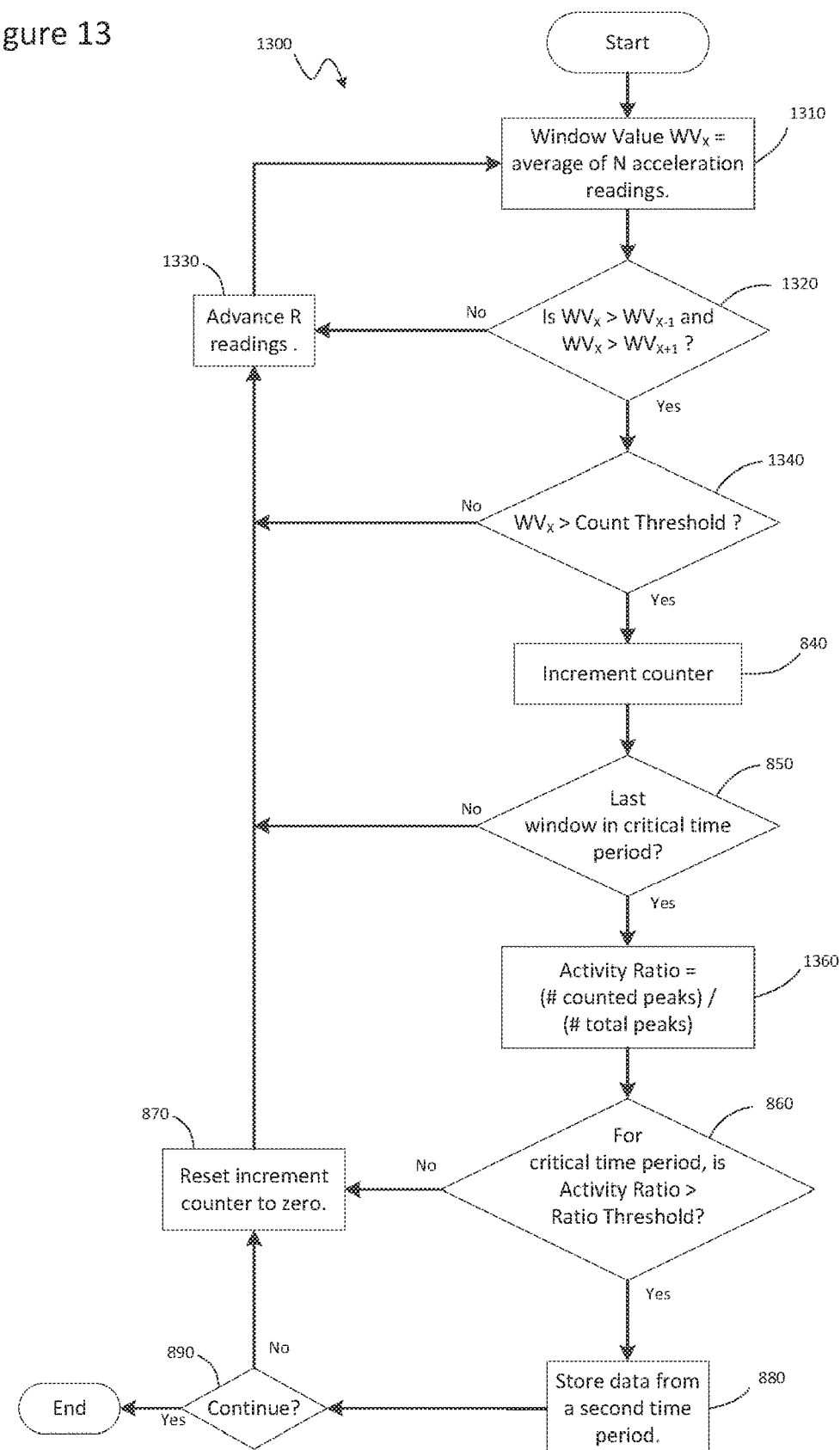
FIG. 13—Embodiment using peak height and separated windows

FIG. 13 presents a flowchart illustrating a method (1300) for selecting accelerometer data to store on a non-transitory computer-readable medium in which using peak height, according to certain embodiments of the present disclosure. Window value for window X ($WV_X$) is the average of N readings (1310). For some embodiments, N may be the number of readings that the accelerometer generates in 1.5 seconds. The method (1300) then determines whether the window value ($WV_X$) is greater than the immediately preceding window value ($WV_{X-1}$) and greater than the immediately following window value ($WV_{X+1}$) (1320). If $WV_X$ is not flanked by lower window values, processing advances R readings (1330) and averages the next window of N readings (1310). In some embodiments, R may equal one and each window advances one reading after the previous window. If $WV_X$ is flanked by lower window values, the method (1300) then queries whether $WV_X$ is greater than a count threshold (1340). Some embodiments, for example, may use a count threshold of 0.625 g. if $WV_X$ is not greater than the count threshold, processing advances R readings (1330) and averages the next window of N readings (1310). If $WV_X$ is greater than the count threshold, the method (1300) increments a counter (840). Then the method (1300) queries whether W is the last window in a critical time period (850). Some embodiments may use a critical time period of one minute. If W is not the last window in the time period, processing advances R readings (1330) and averages the next window of N readings (1310). If W is the last window in the critical time period, the activity ratio is the ratio of the number of counted peaks (the number stored by the increment counter) to the total number of peaks in the critical time period (1360). The method (1300) then queries whether the activity ratio for the critical time period is greater than a activity threshold (860). Some embodiments, for example, use an activity threshold of 0.8. If the activity ratio does not exceed the activity threshold, the increment counter is reset to zero (870), processing advances R readings (1330), and averages the next window of N readings (1310). If the activity ratio exceeds the activity threshold, data from a second time period is stored on the non-transitory computer readable medium (880). The method (1300) then queries whether to continue (890). If so, the increment counter is reset to zero (870), processing advances R readings (1330), and averages the next window of N readings (1310). If not, the method (1300) ends.

Figure 14:
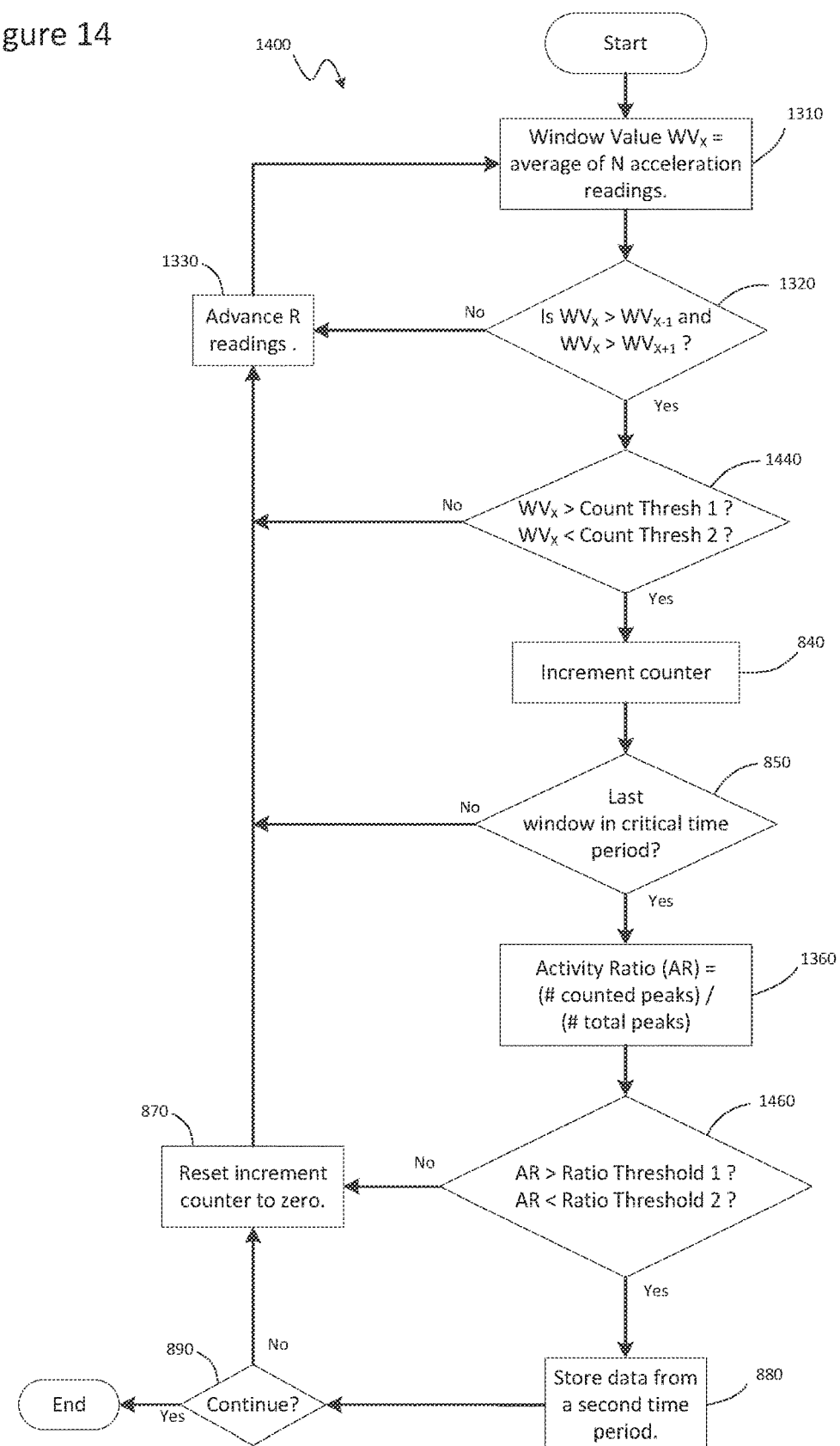
FIG. 14—Embodiment using amplitude and contiguous windows

FIG. 14 presents a flowchart illustrating a method (1400) for selecting accelerometer data to store on a non-transitory computer-readable medium in which using peak height, according to certain embodiments of the present disclosure. Window value for window X ($WV_X$) is the average of N readings (1310). The method (1400) then determines whether the window value ($WV_X$) is greater than the immediately preceding window value ($WV_{X-1}$) and greater than the immediately following window value ($WV_{X+1}$) (1320). If $WV_X$ is not flanked by lower window values, processing advances R readings (1330) and averages the next window of N readings (1310). If $WV_X$ is flanked by lower window values, the method (1400) then queries whether $WV_X$ is both greater than a first count threshold and less than a second count threshold (1440). If $WV_X$ s not between the first and second count thresholds, processing advances R readings (1330) and averages the next window of N readings (1310). If $WV_X$ is between the first and second count thresholds, the method (1400) increments a counter (840). Then the method (1400) queries whether W is the last window in a critical time period (850). If W is not the last window in the time period, processing advances R readings (1330) and averages the next window of N readings (1310). If W is the last window in the critical time period, the activity ratio is calculated as the ratio of the number of counted peaks (the number stored by the increment counter) to the total number of peaks in the critical time period (1360). The method (1400) then queries whether the activity ratio for the critical time period is greater than a first activity threshold and less than a second activity threshold (1460). If the activity ratio is not between the first and second activity thresholds, the increment counter is reset to zero (870), processing advances R readings (1330), and averages the next window of N readings (1310). If the activity ratio is between the first and second activity thresholds, data from a second time period is stored on the non-transitory computer readable medium (880). The method (1400) then queries whether to continue (890). If so, the increment counter is reset to zero (870), processing advances R readings (1330), and averages the next window of N readings (1310). If not, the method (1400) ends.

Gait Analysis

For some embodiments, the accelerometer readings selected for storage on the computer readable medium are subsequently analyzed by a processor to estimate one or more gait parameters. When the activity ratio meets the one or more criteria, systems analyze readings generated during the critical time period to identify steps taken. Readings generated during critical time periods in which the activity ratio does not satisfy the one or more criteria are not analyzed as these critical time periods are less likely to contain step activity.

Individuals propel themselves on foot in a variety of ways including walking, running, and ascending or descending stairs or sloped surfaces. Gait may be assessed in terms of a gait cycle, also called a stride. A stride begins when a reference foot (either the left or right) makes contact with the ground and ends when it next contacts the ground. A stride requires three instances when one of the feet makes contact with the ground two contacts by the reference foot and one contact made by the opposite foot. During the stride, the reference foot spends some time in contact with the ground (called stance) and some time apart from the ground and moving forward (called swing). Both swing and stance of each foot are required to move forward.

A stride is composed of two steps. A step is the action occurring in the interval from the moment that one foot contacts the ground to the moment when the other foot contacts the ground. Step duration is not simply the stance time of one foot. During a walking stride, some time may be spent with both feet touching the ground (called double limb stance) and during a running stride, some time may be spent with neither foot on the ground. Thus, the stance times of each foot may add to more than duration of a walking stride and/or less than the duration of a running stride.

A step may be attributed to either the left foot or the right foot, though actions of both feet are necessary to take a step. A step is often attributed to the foot that is off the ground and moving forward during the step interval. However, steps taken on a gait mat or other instrument may be attributed to the foot touching the mat at the beginning of the step interval.

Steps have attributes sometimes referred to as gait parameters. Step duration is one such parameter and is defined by the beginning and end points of the step. Step frequency is the number of steps taken within a given time period and is the reciprocal of the average step duration during the time period. Step length is the component of the distance between the contact points defining the beginning and end of the step that is in the direction the individual is moving. The walking speed of an individual may be calculated by multiplying step length by step frequency. (Walking, as used herein, may refer to any step-taking activity including, but not limited to, walking, running, ascending, or descending.) Step width is the component of the distance between the contact points that is perpendicular to the direction the individual is moving in the plane of the ground. (Ground, as used herein, refers to any surface on which an individual takes steps and includes, without limitation, floors, stairs, pavement, and natural terrains.)

The portion of a step in which an individual supports his or her weight on a single leg may be referred to as single limb support (SLS) and the portion in which weight is supported on both limbs may be referred to as double limb support (DLS). During DLS, weight may not be supported equally by the legs and DLS may be distinguished from double limb stance which refers to the portion of the step during which both feet are touching the ground. In contrast, when only one foot is in contact with the ground, weight is presumed to be supported by the grounded foot, so there is no need to distinguish between single limb support from single leg stance. The proportions of each step spent in DLS and SLS may be indicative of gait health. In particular, longer periods of DLS may indicate difficulty taking steps. Some gait analysts classify every moment in the gait cycle as either SLS or DLS while others have a third category for transition between SLS and DLS. Under either classification system, both SLS and DLS may be indicative of general health and gait health in particular.

Gait analysis has been used not only to document gait abnormalities but also to determine the underlying causes of the abnormalities and, in some cases, to recommend a treatment. Gait analysis has traditionally been performed in a gait analysis laboratory. Instruments used to perform gait analysis detect a variety of measures associated with walking. However, laboratory-based gait-measuring equipment tends to be expensive, requires that subjects travel to the laboratory, and observes subjects for only the limited time that they are present at the laboratory. The benefits of gait analysis would be available to more patients if it could be conducted using less expensive equipment and the conclusions drawn from gait analysis would be more robust if clinicians could observe patients outside of the laboratory and over longer time periods.

In recent years, accelerometers have become smaller, cheaper, more accurate, and more energy efficient. An accelerometer may refer to a device that measures either linear or angular acceleration. However, accelerometers measuring angular acceleration may also be called gyroscopes, gyrometers, or simply gyros. An accelerometer may also refer to a device that measures acceleration in more than one direction. Triaxial accelerometers have three axes that are at least approximately orthogonal to one another. The output readings from accelerometers may be plotted over time and can be viewed as a signal.

While coupling an accelerometer to a user's hip or leg may yield informative data regarding gait, many users prefer wearing accelerometers elsewhere. Wrist-worn accelerometers have become popular among consumers and may allow for observation of data among a greater number of users and for a greater proportion of the day than accelerometers worn on the hip or leg. However, wrist-worn accelerometers present challenges with respect to inferring gait parameters from the acceleration data.

System embodiments may determine one or more gait parameters using a variety of methods. Some method embodiments estimate gait parameters using accelerometer data from an accelerometer coupled to a user's wrist or another part of the user's arm. An arm may approximate a line segment swinging on the pivot point of the shoulder. Typically, individuals under ordinary conditions swing one of their arms once per stride. That is, the arm returns to its starting position and direction once every two steps. The amount of forward arm swing, as measured by either angle or arc length, may be different than the amount of backward arm swing.

During a cycle of an arm swing, combined linear acceleration may reach a minimum at both the end of a forward arm swing and at the end of a backward arm swing, in each case when the angle of the arm relative is momentarily fixed. Conversely, the maximum combined accelerations during a stride may occur when the arm is mid-swing and approximately parallel to the force of gravity. There are often two peaks per stride one during the forward arm swing and one during the backward arm swing. The moment at which a foot makes contact with the ground corresponds approximately to a minimum acceleration of an arm. The foot that is on the same side as a wrist-worn accelerometer makes contact at approximately the end of the backward arm swing and the foot opposite the side of the accelerometer makes contact at approximately the end of the forward arm swing.

Figure 15:
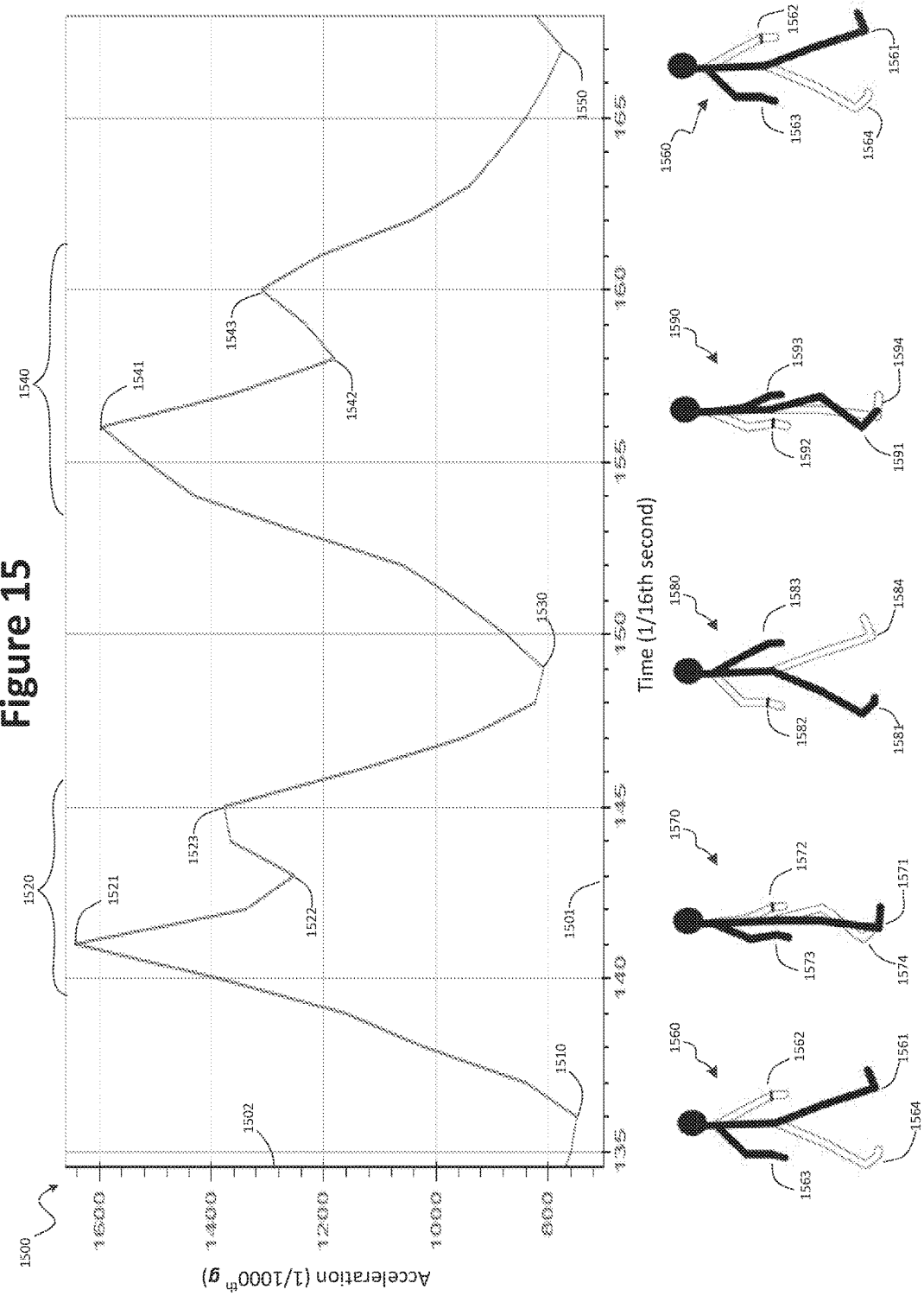
FIG. 15 presents a plot of the magnitude of acceleration of a wrist-worn accelerometer during two steps and presents figures illustrating limb positions corresponding to the acceleration readings.

FIG. 15 presents a sample of acceleration data (1500) from a user's wrist-worn accelerometer while taking two steps. The stick figures 1560, 1570, 1580, 1590) illustrate the position of the user's limbs corresponding to peaks and valleys in the data. The x axis (1501) represents time in $\frac{1}{16}^{th}$ second increments and the y axis (1502) corresponds to the combined magnitude of acceleration in $\frac{1}{1000}$ of g, increments along the axes of a triaxial accelerometer. Each of the two steps comprises a peak (1520, 1540) which is separated from adjacent peaks by three valleys (1510, 1530, 1550). The peak for each of the steps (1520, 1540) is bifurcated into two sub-peaks (1521, 1523, 1541, 1543). Within each peak, the two sub-peaks are separated from one another by a trough (1522, 1542). The cause of these bifurcations is unknown, but they appear typical of most walking data from wrist-worn accelerometers.

In FIG. 15, each of the stick figures 1560, 1570, 1580, 1590) illustrate the position of the limbs corresponding to the acceleration reading of the peak or valley above the particular stick figure. The first step begins when the user's fight heel (1561) first contacts the ground. At this moment, the arm with the accelerometer (the left arm, 1562) is momentarily motionless as the direction of arm swing changes and the combined acceleration at the wrist is approximately that of gravity (g). This corresponds to the valley (1510) that is approximately at g (800/1000 g). The right arm (1563) is in the back-most position of its swing and the left leg (1564) is pushing off of the left foot. Peak (1520) occurs when the arm with the accelerometer (the left arm, 1572) is mid-swing and pointing approximately parallel to the force of gravity as it swings backward. The right arm (1573) is also mid-swing and approximately parallel to gravitational force. Weight is supported on the right leg (1571) as the left leg (1574) is swinging. The first step ends and the second step begins when the left heel (1584) contacts the ground. The left arm (with accelerometer, 1582) is motionless at the back-most portion of its swing and the accelerometer registers only the force of gravity corresponding to valley (1530). The right arm (1583) is at the forward-most part of its swing and the right leg (1581) is pushing off the ground. Peak (1540) occurs when the arm with the accelerometer (the left arm, 1592) is mid-swing and pointing approximately parallel to the force of gravity as it swings forward. The right arm (1593) is also mid-swing and approximately parallel to gravitational force. Weight is supported on the left leg (1591) as the right leg (1594) is swinging. The second step ends when the left heel (1564) contacts the ground as it did for the first step.

Gait Speed

The rate at which an individual moves on foot, gait speed, may be computed as the ratio of step length to step duration the amount of time from the beginning of a step to the end of the step. Embodiments estimating gait speed estimate both step length and step duration.

Step Duration

A step begins at the moment that one of the feet first makes contact with the ground and ends at the moment the other foot next contacts the ground. Since foot contact occurs at approximately the moment that the arms have reached the end of their respective swings, combined acceleration along the x and y axes of an accelerometer reaches a minimum at the time one step ends and the next begins. Step duration (SD) may therefore be estimated as the time between two step minima those acceleration minima corresponding to the end point of an arm swing as opposed the trough between the sub-peaks or other local minima caused by noise in the data. A minimum may refer to an accelerometer reading that is flanked on both sides by higher readings; the reading immediately preceding a minimum and the reading immediately following a reading are each greater than the minimum data point.

Figure 16:
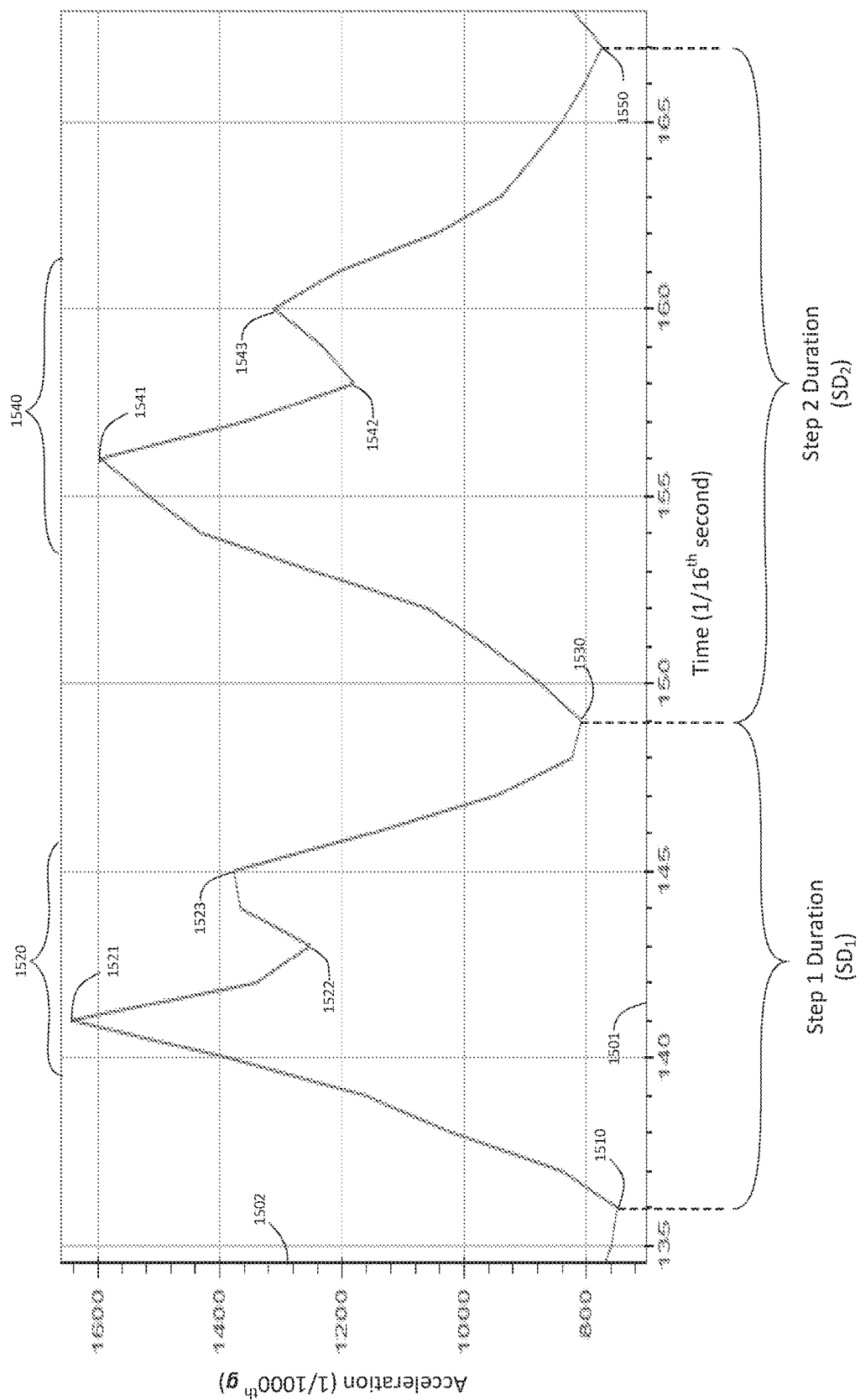
FIG. 16 presents a plot of acceleration of a wrist-worn accelerometer during two steps and illustrates the duration of each step as estimated by features of the accelerometer data, according to certain embodiments of the present disclosure.

FIG. 16 presents the acceleration plot of FIG. 15 with duration of the first and second steps ($SD_1$ and $SD_2$, respectively) indicated by brackets. Step duration may be estimated as the difference between the time at which one step minimum occurred and the time at which the next step minimum occurred. In FIG. 16, the first step begins at the minimum (1510) occurring at approximately 136 16ths of a second and ends at the minimum (1530) occurring at approximately 149 16ths of a second. Thus, $SD_1$=(149−136)/16 of a second or $^{13}/_{16}$ths of a second. Step 2 begins at 149 16ths of a second and ends at the minimum (1550) occurring at approximately 167 16ths of a second. SD2= (167−149)/16 of a second or $^{19}/_{16}$ths of a second.

To determine the duration of a particular step via processor implemented instructions, some embodiments analyze accelerometer data as a "sliding window." A data window (window) refers to a group of accelerometer readings (also called data points) generated at a given amount of time relative to a reference data point. The readings in a window are considered in an analysis. For example, some embodiments analyze data generated in the half second before the reference data point. If analysis takes place in real time, the reference data point may be the most recently generated data point. But post-hoc analysis may use a past reference data point that progresses to another reference data point (also referred to as a focal data point) once the window associated with the first data point has been analyzed. The window "slides" in that the reference data point advances by one reading (or a number of readings less than the number of readings in the window) for each analysis. Thus, for sliding windows advancing by a single data point from one analysis to the next, the group of readings being analyzed differs by only the first and last data points in the window; the first data point is new and the last data point is no longer part of the group considered. Some windows may slide by advancing more than one data point at a time provided there is at least one common data point between two windows. Some embodiments use contiguous windows (in which the first data point in a window is the reading immediately following the last data point of the previous window) and some embodiments use separated windows (in which windows are separated by unanalyzed data points.

Some embodiments adjust window size as a function of acceleration data. For example, some embodiments analyze a window that is approximately half the duration of the fundamental frequency determined by an autocorrelation function. (Note that the autocorrelation function may yield the typical step duration over a period of time but does not determine the duration of a particular step.) If halving the duration yields a fractional number of data points, some embodiments may, for example, round down to the time period with the next lowest whole number of data points.

Some embodiments use sliding windows as a tool to distinguish step minima (those marking the farthest point of an arm swing) from other local minima. A local minimum may refer to a downward inflection point an acceleration reading flanked on both sides by higher readings. For example, some embodiments count a point as a step minimum only if is the lowest reading in the window that is flanked by higher points. For these embodiments, determining an appropriate window size is important to identify steps. If a window is too long, steps may be missed and if the window is too short, local minima that are not steps may be counted as such. After identifying the step minima in the acceleration signal, the time between each identified step minimum may approximate the time for an individual step.

Figure 17:
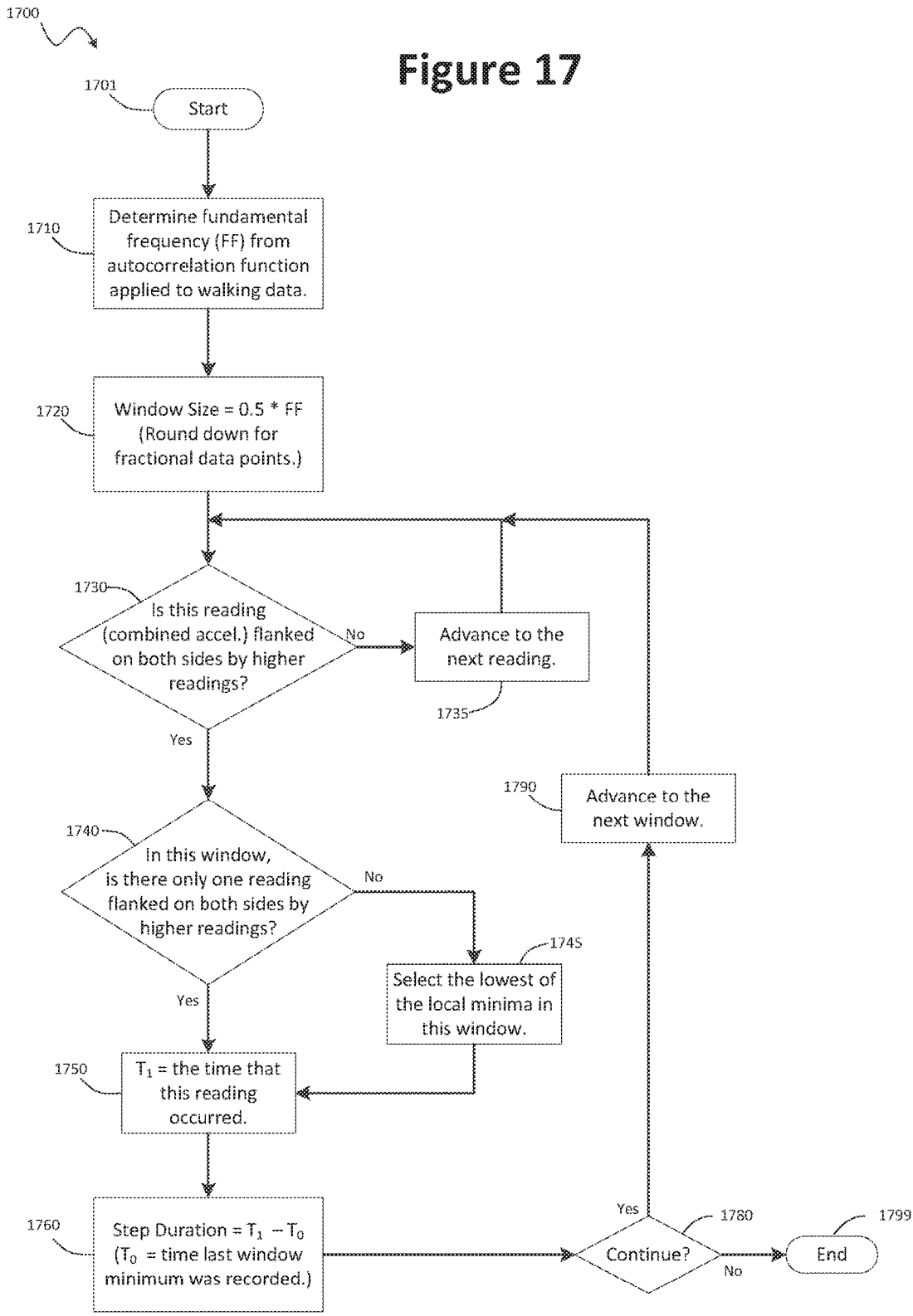
FIG. 17 presents a flow chart illustrating an accelerometer-based method for estimating step duration, according to certain embodiments of the present disclosure.

FIG. 17 presents a flow chart illustrating a computer-implemented method (1700) of determining step duration, according to certain embodiments. After the start (1701), the fundamental frequency from an autocorrelation function is determined (1710). Window size is set at half the fundamental frequency of the autocorrelation (1720). If half the time of the fundamental frequency includes a fraction of an accelerometer reading, the window size rounds down to the next whole number of readings (1720). Starting with the first reading in a window, the method (1700) queries whether the reading is lower than both the immediately previous reading and the immediately following reading (1730). If not, analysis proceeds to the next reading (1735). If the reading is a local minimum (flanked by greater readings), the method then queries whether the reading is the only local minimum in its window (1740). If so, the single local minimum is selected. If there are one or more other local minima in the window, the lowest of the local minima is selected (1745). The time of the selected local minimum ($T_1$) is then accessed (1750). Step duration is estimated as the time between $T_1$ and $T_0$—the time at which the previous step minimum occurred (1760). The method (1700) then queries whether to continue (1780). If so, analysis proceeds to the next window (1790). If not, the method (1700) ends (1799).

Step Length

Determining step length from wrist-wont accelerometer data has proven challenging, particularly when data on angular acceleration is absent. Some embodiments calculate step length as a function of the distance the hand travels when swinging during a step.

Figure 18:
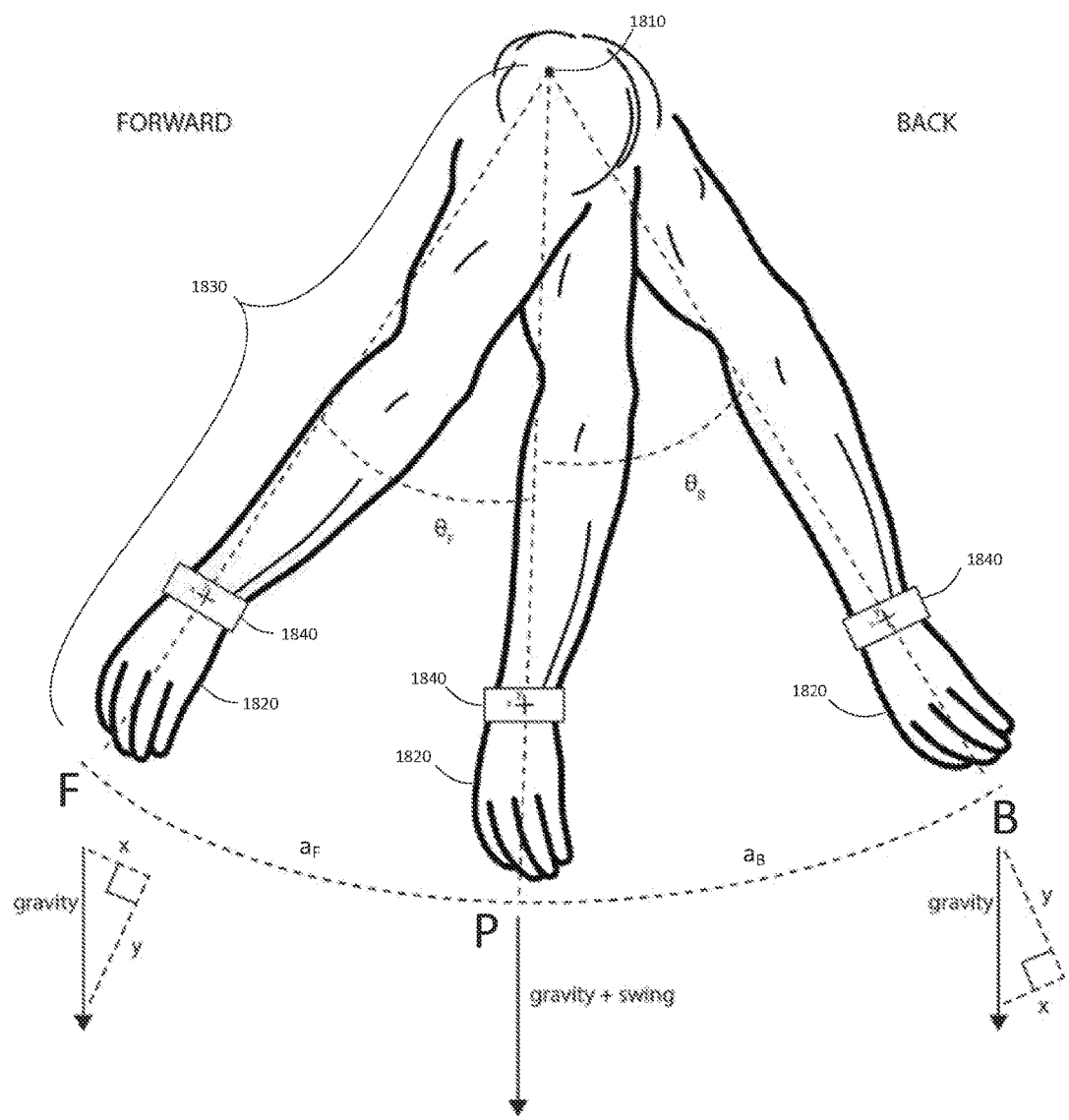
FIG. 18 presents a schematic diagram illustrating the changing orientation of an accelerometer on a swinging arm, relative to gravity.

FIG. 18 illustrates arm position as a simple line segment pivoting around a point. The shoulder (1810) is the pivot point and the hand (1820) functions as the end of the line segment. The arm from shoulder to hand is represented as a dashed line segment (1830) having a length of L. An accelerometer (1840) having two orthogonal axes (x and y) is coupled to the wrist. In position P, the arm is parallel to the direction of gravity. Position F is the forward-most position of the arm during a swing and position B is the back-most position of the arm. The angle of arm swing between position P and position F is labeled $\theta_F$ and the angle of arm swing between position P and position B is labeled $\theta_B$. The arc length, the distance the hand travels from position P to position F, may be referred to as $a_F$ and the arc length the hand travels from position P to position B, may be referred to as $a_B$. $a_F$ may be calculated as $\theta_F * L$ and $a_B$ may be calculated as $\theta_B * L$ where $\theta_F$ and $\theta_B$ are measured in radians.

As FIG. 18 illustrates, the force of gravity acts like a constant acceleration in the direction opposite gravitational pull. In position P, downward force is caused both by gravity and the centripetal force of the arm swinging on its axis. In positions F and B, when the arm is momentarily stationary, gravity is the primary force acting on the accelerometer. Some embodiments determine values for $\theta_F$ and $\theta_B$ by measuring the components of gravitational pull on the x and y axes of an accelerometer at positions F and 13, respectively. For example, some embodiments measuring acceleration along x and y axes may calculate either $\theta_F$ or $\theta_B$ as the arctangent of the ratio of force along the x axis to force along the y axis or as the arccosine of the ratio of acceleration along the y axis to total gravitational pull. If step length is calculated as a function of total arm swing (the sum of $a_F$ and $a_B$), the method need not distinguish whether the arm swing is in the forward ($a_F$) or backward ($a_B$) direction. Some embodiments measuring acceleration along three axes determine $\theta$ as a function of how gravitational pull is distributed among the three axes and may compensate for the accelerometer rotating about the wrist as the arm swings.

The arc length that the hand travels during an arm swing is a function of the sum of $a_F$ and $a_B$ ($a_{total}$) and the length of the user's arm (L). Some embodiments use a standard length for L. 'The standard may be a global measure of central tendency for arm length or may be informed by factors such as the user's height, age, gender, or an actual measurement of the user's arm. As explained for FIG. 18, total arc length ($a_{total}$) may be calculated, for example, as $\theta_{total}*L$ where $\theta_{total}$ is measured in radians. Some embodiments calculate step length as equal to the arc length of arm swing. Some embodiments calculate step length as a function of the arc length of arm swing. For example, some embodiments may multiply the arc length of arm swing by a coefficient to obtain step length.

Figure 19:
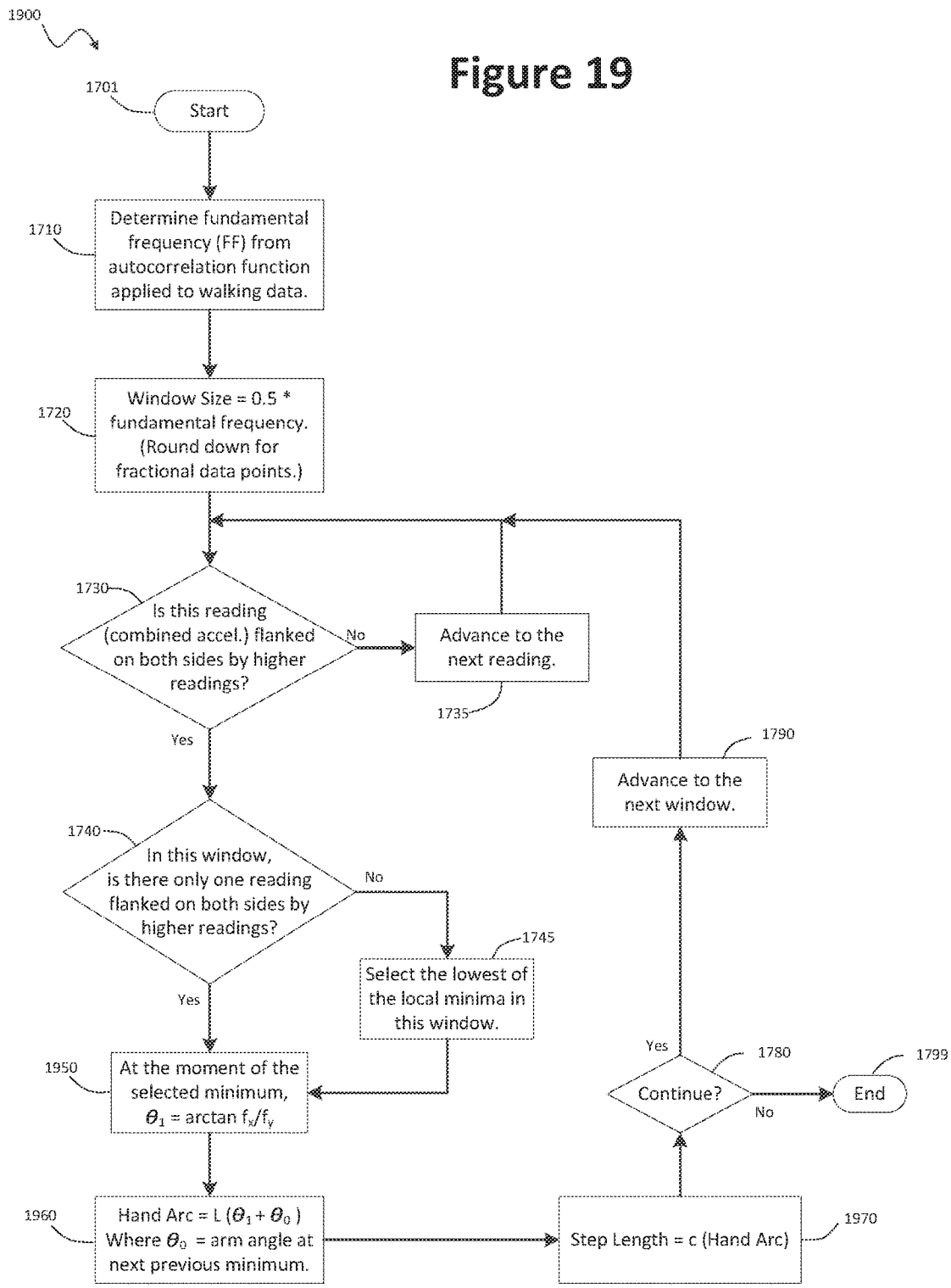
FIG. 19 presents a flow chart illustrating an accelerometer-based method for estimating step length, according to certain embodiments of the present disclosure.

FIG. 19 is a flow chart illustrating a method (1900) for estimating step length, according to certain embodiments. After the start (1701), the fundamental frequency (FF) for a sample of data using an autocorrelation function is determined (1710). Window size is set at half the fundamental frequency of the autocorrelation (1720). If half the time of the fundamental frequency includes a fraction of an accelerometer reading, the window size rounds down to the next whole number of readings (1720). Starting with the first reading in a window, the method (1900) queries whether the reading is lower than both the immediately previous reading and the immediately following reading (1730). If not, analysis proceeds to the next reading (1735). If the reading is a local minimum (flanked by greater readings), the method then queries whether the reading is the only local minimum in its window (1740). If so, the single local minimum is selected. If there are one or more other local minima in the window, the lowest of the local minima is selected (1745). Once a minimum is selected, arm angle $\theta_1$ (the method does not distinguish whether the arm swing is in the forward or backward direction) may be calculated as arctangent of the ratio of measured acceleration along the accelerometer's x axis ($f_x$) to measured acceleration along the accelerometer's y axis ($f_y$) (1950). Next, hand arc length is calculated by multiplying the sum of $\theta_1$ and $\theta_0$ (each expressed in radians) by the length of the user's arm (L) (1960), $\theta_0$ is the arm angle calculated for the immediately previous combined acceleration minimum. Step length is estimated as the hand arc length of the arm swing multiplied by a constant c (1970). The method (1900) then queries whether to continue (1780). If so, analysis proceeds to the next window (1790). If not, the method (1900) ends (1799).

Single and Double Limb Support

Single limb support (SLS) and double limb support (DLS) may be important measures for assessing gait health. Those with balance disorders or other difficulties walking tend to exhibit a higher proportion of their gait cycle in DLS and a lower proportion in SLS. Some embodiments estimate SLS and/or DLS through processor-implemented analysis of an acceleration signal wherein the accelerometer is attached to the arm of a user. In some embodiments, the accelerometer may be a triaxial accelerometer and the processor analyses the combined magnitude of acceleration from all three axes.

Figure 20:
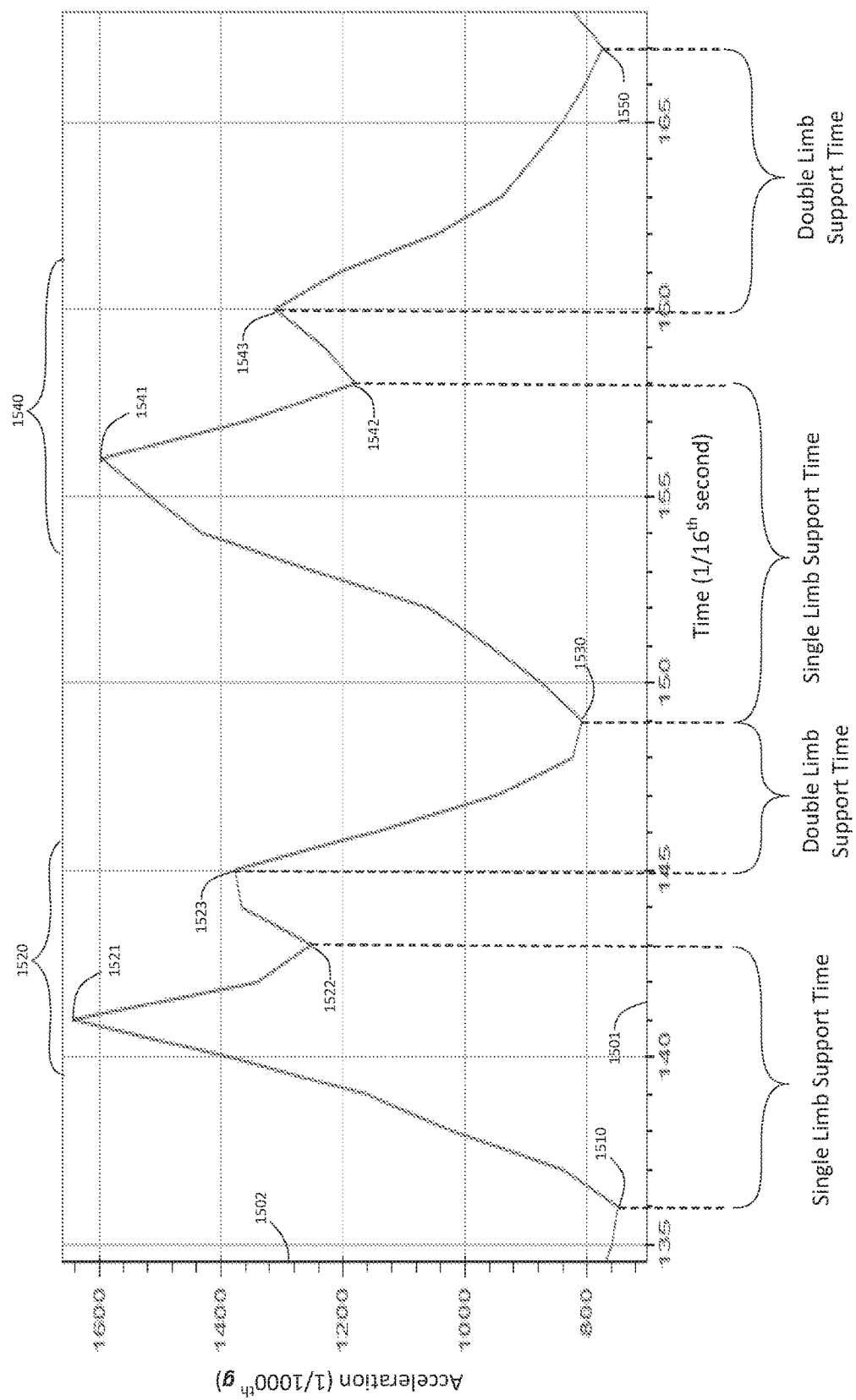
FIG. 20 presents a plot of acceleration of a wrist-worn accelerometer during two steps and illustrates the portion of each step attributed to SLS and to DLS according to certain embodiments of the present disclosure.

FIG. 20 presents the acceleration plot of FIG. 15 and delineates time periods corresponding to the durations of both SLS and DLS, according to certain embodiments. The specified time periods may not correspond exactly to the times when SLS and/or DLS is occurring but estimate the amount of time spent in each state. In this embodiment, the times for SLS and DLS do not add to the total step duration (SD). Time in a step not spent in SLS or DLS may be referred to as the transitional phase of a step. For each of the two steps, the embodiment estimates the duration of SLS as the time from the step minimum marking the beginning of the step (1510, 1530) to the local minimum separating the two sub-peaks of the step (1522, 1542, respectively). SLS time for the first step ($SLS_1$) time is estimated as being the amount of time from step minimum 1510 to local minimum 1522 which is approximately 7/16ths of a second. The proportion of the first step spent in SLS is estimated to be $SLS_1/SD_1$ or 8/13ths of the step. Likewise, SLS time for the second step ($SLS_2$) is estimated as the amount of time from step minimum 1530 to local minimum 1542 which is approximately 9/16ths of a second. The proportion of the second step spent in SLS is estimated to be $SLS_2/SD_2$, or 9/18ths (half) of the step. For each of the two steps shown in the plot, the duration of DLS is estimated to be the time from the second sub-peak of the step (1523, 1543) to the step minimum marking the end of the step during which the sub-peaks occurred (1530, 1550, respectively). DLS time for the first step ($DLS_1$) is estimated as being the amount of time from sub-peak 1523 to step minimum 1530 which is approximately 4/16ths (one quarter) of a second. The proportion of the first step spent in DLS is estimated to be $DLS_1/SD_1$ or 4/13ths of the step. Likewise, DLS time for the second step ($DLS_2$) is estimated as the amount of time from sub-peak 1543 to step minimum 1550 which is approximately 7/16ths of a second. The proportion of the second step spent in DLS is estimated to be $DLS_2/SD_2$, or 7/18ths of the step.

Similar to embodiments described for estimating step duration, some processor-implemented embodiments determine a time duration for a first sliding window. Some embodiments use a predetermined time span for the sliding window. For example, some embodiments analyze data generated in the third (1/3) of a second before the reference data point while some analyze data generated in the half (0.5) of a second before the reference data point. However, some embodiments adjust the window size as a function of acceleration data. For example, some embodiments analyze data points in a window that is approximately half the fundamental frequency determined by an autocorrelation function applied to accelerometer walking data. If halving the fundamental frequency yields a fractional number of data points, some embodiments may, for example, round up or down to the time period with the next lowest whole number of data points.

Some embodiments use sliding windows to identify beginning and end points of steps. A step may occur between two step minima where a step minimum refers to one that takes place when the arm has reached the end of its swing, either in the forward or backward positions. Some embodiments count a point as a step minimum only if is the lowest local minimum (a reading flanked on both sides by greater readings) in the window.

Some embodiments may determine a second sliding window that is shorter than the first sliding window. The second sliding window may serve to identify the trough separating the sub-peaks in a peak. As with the first sliding window, the second sliding window may, for example, be a fixed duration or may be a function of accelerometer readings. An embodiment may, for example, use a fixed duration of a quarter of a second. Alternatively, an embodiment may set the second sliding window as, for example, a quarter of the fundamental frequency determined by an autocorrelation function. Peaks and troughs, as defined by the second sliding window, are the highest local maximum (flanked on both sides by lower points) and the lowest local minimum (flanked on both sides by higher points) within a window.

Some embodiments calculate SLS time as the amount of time from a valley as determined according to the first sliding window to the next trough as determined by the second, shorter, sliding window. Within an episode of walking walk), the average SLS time per step may be calculated as the cumulative SLS time for a number of steps divided by the cumulative step duration for those steps. Some embodiments screen the data by discarding estimates for steps in which there are not at least two peaks and three valleys between two adjacent valleys as determined by the first (longer) sliding window.

Figure 21:
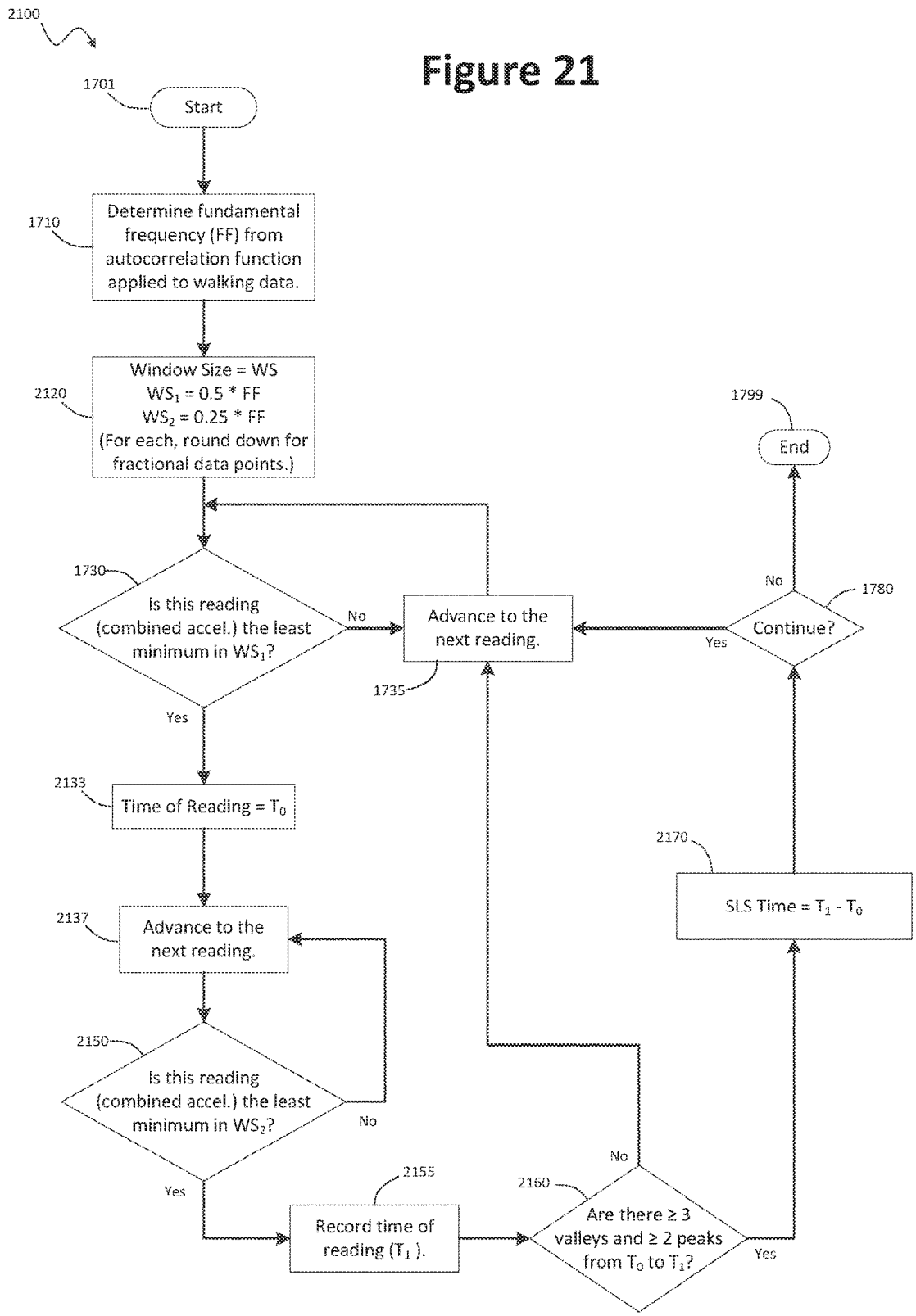
FIG. 21 presents a flow chart illustrating a method for estimating SLS duration, according to certain embodiments of the present disclosure.

FIG. 21 presents a flow chart illustrating an embodiment of a processor-implemented method (2100) for estimating SLS. After the start (1701), the fundamental frequency (FF) for a sample of data (combined acceleration of all axes) using an autocorrelation function is determined (1710). Windows of two sizes are selected; $WS_1$ is half (0.5) of and $WS_2$ is one quarter (0.25) FF (2120). For both windows, window duration is rounded down to the next lowest whole number of accelerometer readings (2120). The method (2100) then queries if the focal reading (the reading being examined) is the lowest local minimum in $WS_1$ (1730). If not, analysis proceeds to the next reading (1735). If the focal reading is the lowest minimum in $WS_1$, the time at which the focal reading was generated ($T_0$) is recorded (2133). Analysis then proceeds to the next reading (2137). The method (2100) then queries if the focal reading is the lowest minimum in $WS_2$ (2150). If not, analysis proceeds to the next reading (2137). If the focal reading is the lowest minimum in $WS_2$, the time at which the focal reading was generated ($T_1$) is recorded (2155). The method (2100) then queries whether there have been at least 3 valleys and two peaks (within the second, shorter window) in the time period from $T_0$ to $T_1$ (2160). If not, analysis proceeds to the next reading (1735). If so, the method (2100) estimates the amount of SLS time to be the difference between $T_1$ and $T_0$ (2170). The fraction of the step spent in SLS is estimated as SLS time divided by step duration (SD) (2170). The method (2100) then queries whether to continue (1780). If not, the method (2100) ends (1799). If analysis continues, analysis proceeds to the next reading (1735) where the method (2100) queries if the focal reading is the lowest minimum in $WS_1$ (1730). Step 1730 effectively scans for the beginning of the next step.

Some embodiments calculate DLS time as the amount of time starting at the second peak as determined by a second (shorter) sliding window to the next valley as determined by the first (longer) sliding window. The "second valley" is the second relative to the beginning of a step defined by a valley determined by the first (longer) sliding window.

Figure 22:
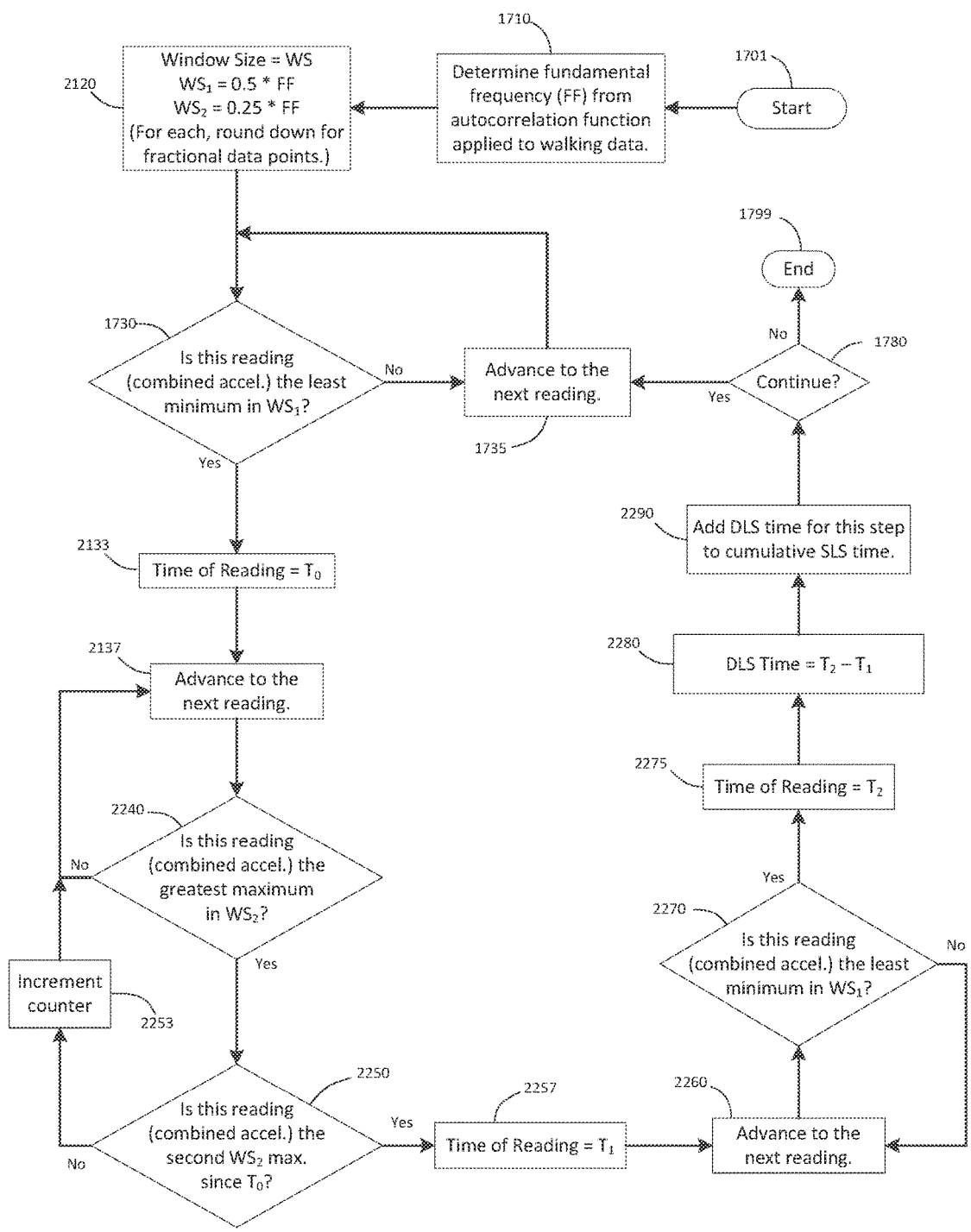
FIG. 22 presents a flow chart illustrating a method for estimating DLS duration, according to certain embodiments of the present disclosure.

FIG. 22 presents a flow chart illustrating an embodiment of a processor-implemented method (2200) for estimating DLS. After the start (1701), the fundamental frequency (FT) for a sample of data using an autocorrelation function is determined (1710). Windows of two sizes are selected; $WS_1$ is half (0.5) of FT and $WS_2$ is one quarter (0.25) FF (2120). For each window, window duration is rounded down to the next lowest whole number of accelerometer readings (2120). The method (2200) then queries if the focal reading (combined acceleration of all axes) is the lowest minimum in $WS_1$ (1730). If not, analysis proceeds to the next reading (1735). If the focal reading is the lowest local minimum in $WS_1$, the time at which the focal reading was generated ($T_0$) is recorded (2133). Analysis then proceeds to the next reading (2137). The method (2200) then queries whether the focal reading is the greatest maximum in $WS_2$ (2240). If the focal reading is not the greatest local maximum in $WS_2$, analysis advances to the next reading (2137). If the focal reading is the greatest maximum in $WS_2$, the method (2200) queries whether the focal reading is the second maximum (within $WS_2$) to occur since $T_0$ (2250). If not, a counter is incremented (2253) and analysis advances to the next reading (2137). If the focal reading is the second maximum (within $WS_2$) to occur since $T_0$, the time of the focal reading is recorded as $T_1$ (2257). Analysis then proceeds to the next reading (2260). The method (2200) then queries whether the focal reading is the least minimum within $WS_1$ (2270). If not, analysis advances to the next reading (2260). If the focal reading is the least minimum within $WS_1$, the time of the focal reading is stored as $T_2$ (2275). DLS time is estimated as the difference between $T_2$ and $T_1$ (2280). The fraction of the step spent in DLS is estimated as DLS time divided by step duration (2280). The amount of DLS time is then added to a cumulative tally of SLS time during the walk (2290) which, when divided by the duration of the walk, yields the average proportion of DLS time for steps taken during the walk. The method (2200) then queries whether to continue (1780). If not, the method (2200) ends (1799). If analysis continues, analysis proceeds to the next reading (1735) where the method (2200) queries if the focal reading is the lowest minimum in $WS_1$, effectively scanning for the beginning of the next step (1730).

Some embodiments estimate SLS and DLS using threshold crossing points in addition to peaks and valleys. One embodiment, for example, estimates DLS time as the time from a valley marking the beginning of a step to the time at which acceleration readings first exceed a threshold. The valley may be determined, for example, by a sliding window. Correspondingly, some embodiments estimate SLS time as starting when accelerometer readings first exceed a threshold and ending at the valley marking the end of a step.

Figure 23:
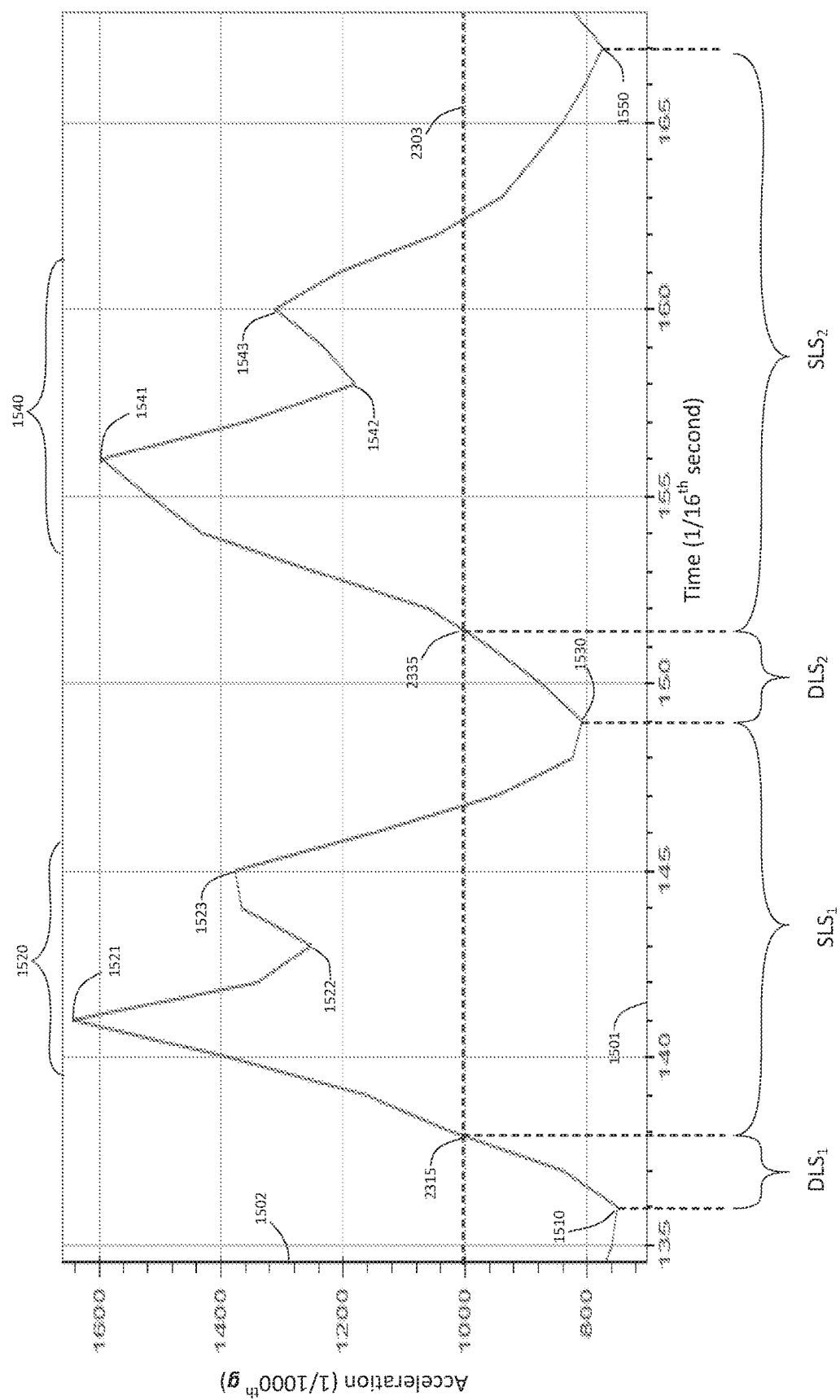
FIG. 23 presents a plot of acceleration of a wrist-worn accelerometer during two steps and illustrates the portion of each step attributed to SLS and to DLS according to certain embodiments of the present disclosure.

FIG. 23 presents the acceleration plot of FIG. 15 and delineates time periods corresponding to the durations of both SLS and DLS, according to certain embodiments. The specified time periods do not necessarily correspond to the times when SLS and/or DLS are occurring. A horizontal dashed line (2303) at gravitational acceleration (g) represents a threshold set at that level. In this embodiment, the times for SLS and DLS add to the total step duration (SD). For each of the two steps shown in the plot, the DLS time is estimated to be the time from the valley marking the beginning of a step (1510, 1530) to the first time (within the step) in which acceleration readings exceed threshold 1503 (2315, 2335 respectively). DLS time for the first step ($DLS_1$) is estimated as being the amount of time from valley 1510 to threshold crossing 2315, which is approximately 2/16ths (one eighth) of a second. The proportion of the first step spent in DLS is estimated to be $DLS_1/SD_1$ or 2/13ths of the step. SLS time for the first step ($SLS_1$) is estimated as being the amount of time from threshold crossing 2315 to valley 1530, which is approximately 11/16ths of a second. The proportion of the first step spent in SLS is estimated to be $SLS_1/SD_1$ or 11/13ths of the step. DLS time for the second step ($DLS_2$) is estimated as the amount of time from valley 1530 to threshold crossing 2335 which is approximately 2.5/piths of a second. The proportion of the second step spent in DLS is estimated to be $DLS_2/SD_2$, or 2.5/18ths of the step. SLS time for the second step ($SLS_2$) is estimated as being the amount of time from threshold crossing 2335 to valley 1550, which is approximately 15.5/16ths of a second. The proportion of the first step spent in SLS is estimated to be $SLS_1/SD_1$ or 15.5/18ths of the step.

Figure 24:
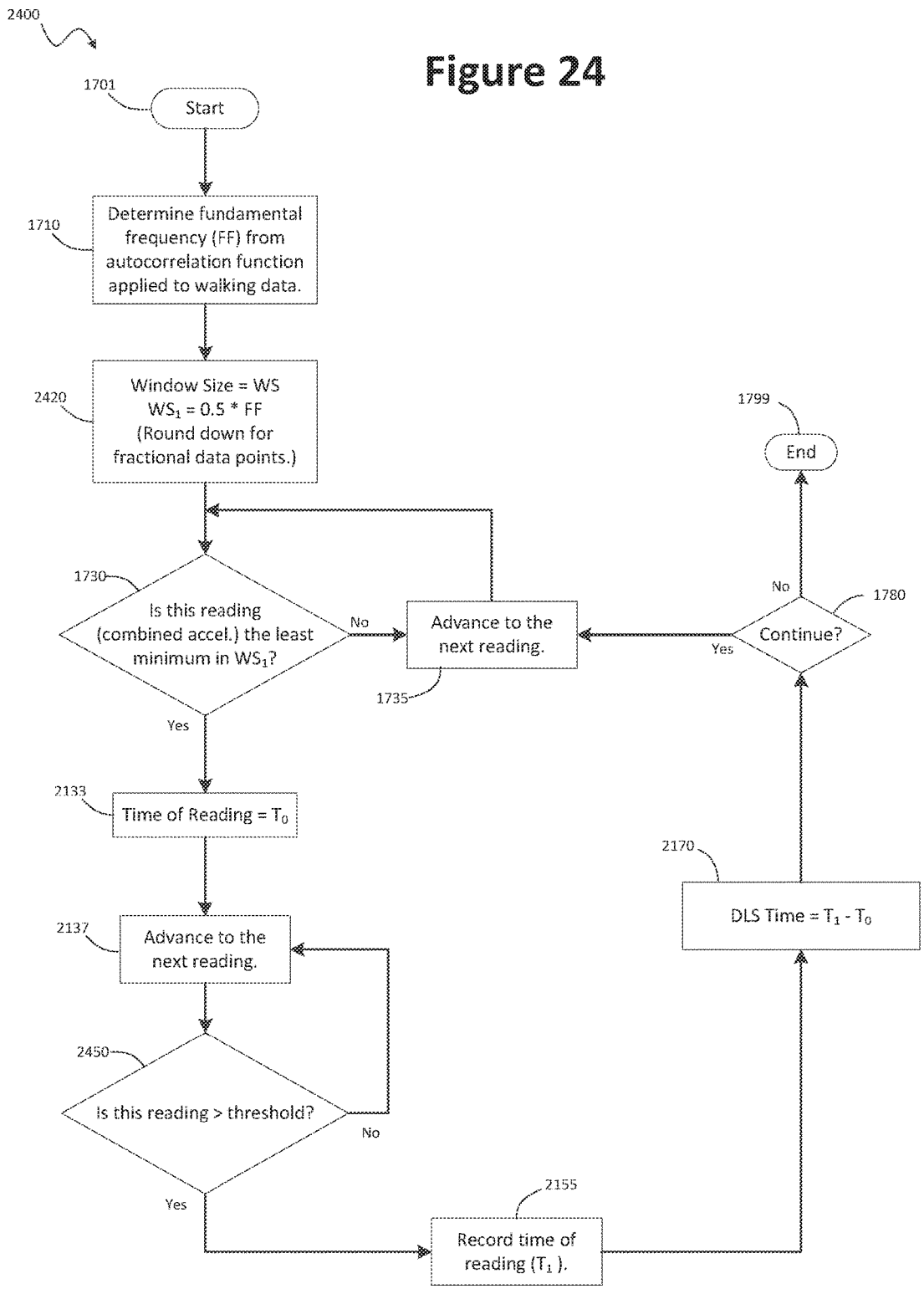
FIG. 24 presents a flow chart illustrating a method for estimating SLS time, according to certain embodiments of the present disclosure.

FIG. 24 presents a flow chart illustrating an embodiment of a processor-implemented method (2400) for estimating DLS. After the start (1701), the fundamental frequency (FF) for a sample of data (combined acceleration of all axes) using an autocorrelation function is determined (1710). Window size $WS_1$ is half (0.5) of FF (2420). Window duration is rounded down to the next lowest whole number of accelerometer readings (2420). The method (2400) then queries if the focal reading (the reading being examined) is the lowest local minimum in $WS_1$ (1730). If not, analysis proceeds to the next reading (1735). If the focal reading is the lowest minimum in $WS_1$, the time at which the focal reading was generated ($T_1$) is recorded (2133). Analysis then proceeds to the next reading (2137). The method (2400) then queries if the focal reading is the greater than a threshold (2450). In some embodiments, the threshold is 1 g. If not, analysis proceeds to the next reading (2137). If the focal reading is greater than the threshold, the time at which the focal reading was generated ($T_1$) is recorded (2155). The method (2400) estimates the amount of DLS time to be the difference between $T_1$ and $T_0$ (2170). The method (2400) then queries whether to continue (1780). If not, the method (2400) ends (1799). If analysis continues, analysis proceeds to the next reading (1735) where the method (2400) queries if the focal reading is the lowest minimum in $WS_1$ (1730). Step 1730 effectively scans for the beginning of the next step.

Figure 25:
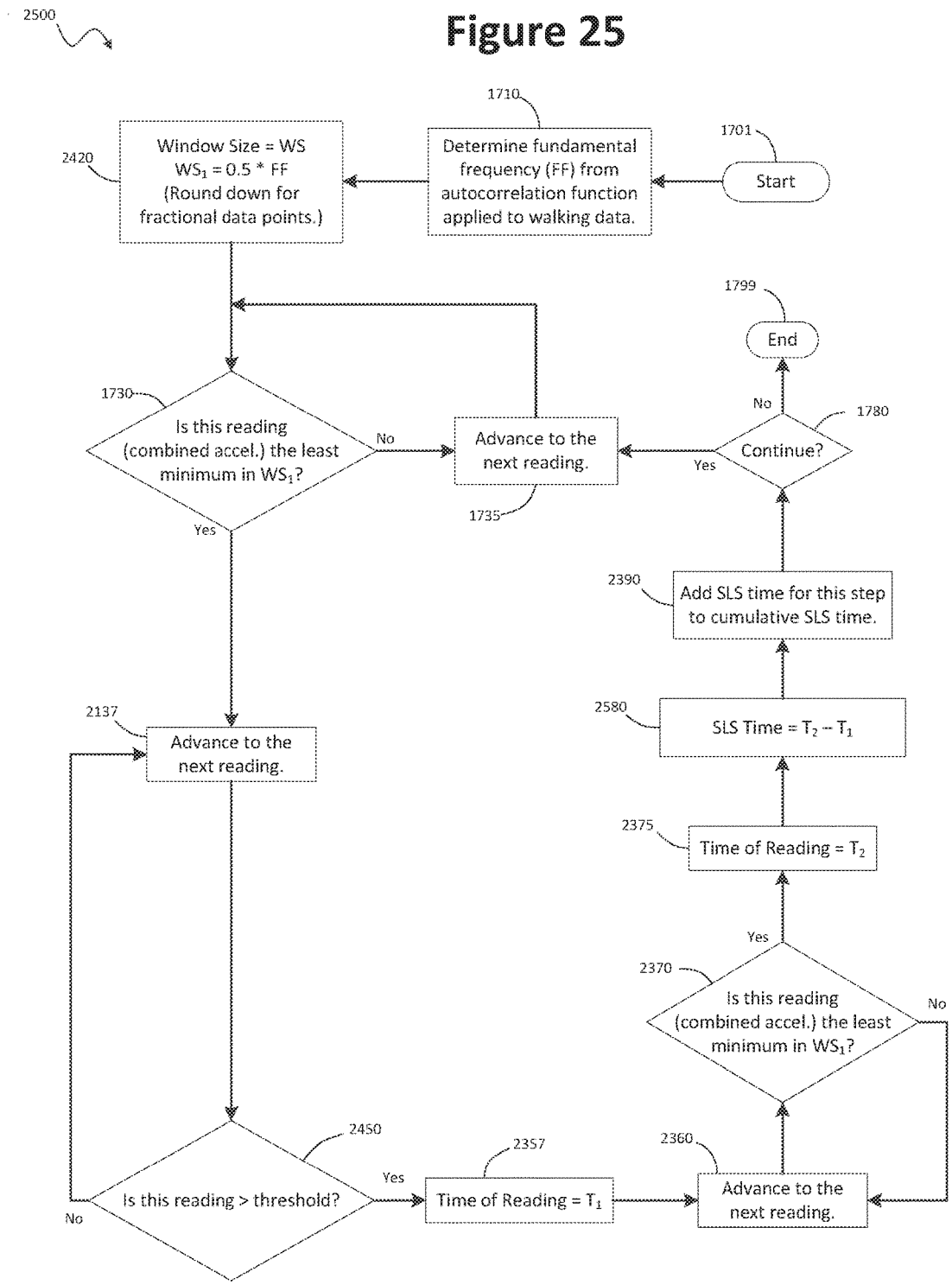
FIG. 25 presents a flow chart illustrating a method for estimating DLS time, according to certain embodiments of the present disclosure.

FIG. 25 presents a flow chart illustrating an embodiment of a processor-implemented method (2500) for estimating SLS. After the start (1701), the fundamental frequency (FF) for a sample of data using an autocorrelation function is determined (1710). Window size $WS_1$ is half (0.5) of FF (2420). Window duration is rounded down to the next lowest whole number of accelerometer readings (2420). The method (2500) then queries if the focal reading (combined acceleration of all axes) is the lowest minimum in $WS_1$ (1730). If not, analysis proceeds to the next reading (1735). If the focal reading is the lowest local minimum in $WS_1$, analysis proceeds to the next reading (2137). The method (2500) then queries whether the focal reading is greater than a threshold (2350). In some embodiments, the threshold is 1 g. If the focal reading is not greater than the threshold, analysis advances to the next reading (2137). If the focal reading is greater than the threshold, the time of the focal reading is recorded as $T_1$ (2357). Analysis then proceeds to the next reading (2360). The method (2500) then queries whether the focal reading is the least minimum within $WS_1$ (2370). If not, analysis advances to the next reading (2360). If the focal reading is the least minimum within $WS_1$, the time of the focal reading is stored as $T_2$ (2375). SLS time is estimated as the difference between $T_2$ and $T_1$ (2580). The amount of SLS time is then added to a cumulative tally of SLS time during the walk (2390) which, when divided by the duration of the walk, yields the average proportion of SLS time for steps taken during the walk. The method (2500) then queries whether to continue (1780). If not, the method (2500) ends (1799). If analysis continues, analysis proceeds to the next reading (1735) where the method (2500) queries if the focal reading is the lowest minimum in $WS_1$, effectively scanning for the beginning of the next step (1730).

Step Width

Step width is the component of the distance between the contact points of the feet that is perpendicular to the direction the individual is moving. Step width may be an important indicator of conditions such as obesity and balance disorders. Some embodiments estimate step width using a double integral of acceleration along an axis approximately parallel to the user's lateral anatomical axis. An integral, or area under the signal curve, may be estimated using a Riemann sum or other techniques known to those in the art. The integral may taken from the beginning of the step to the end of the step as determined by lowest minima in a data window. Of these embodiments, some estimate step width as a function of the double integral. For example, some of these embodiments multiply the double integral by a coefficient selected to accommodate the particularities of a specific accelerometer or type of accelerometer.

Some embodiments screen data on a Z axis to determine whether the data should be discarded from consideration. For example, some embodiments do not estimate width of a particular step if readings on a Z axis of the accelerometer exceed a threshold. Readings from the Z axis exceeding a threshold may indicate that part of acceleration in the direction of the Z axis is caused by rotation of the wrist or rotation of the accelerometer about the wrist.

Once estimated, step width may be used with other estimated measures. For example, some embodiments calculate a step ratio the ratio of step length to step width. Step ratio may be more informative than step width alone since step width tends to increase with step length even among healthy individuals.

Figure 26:
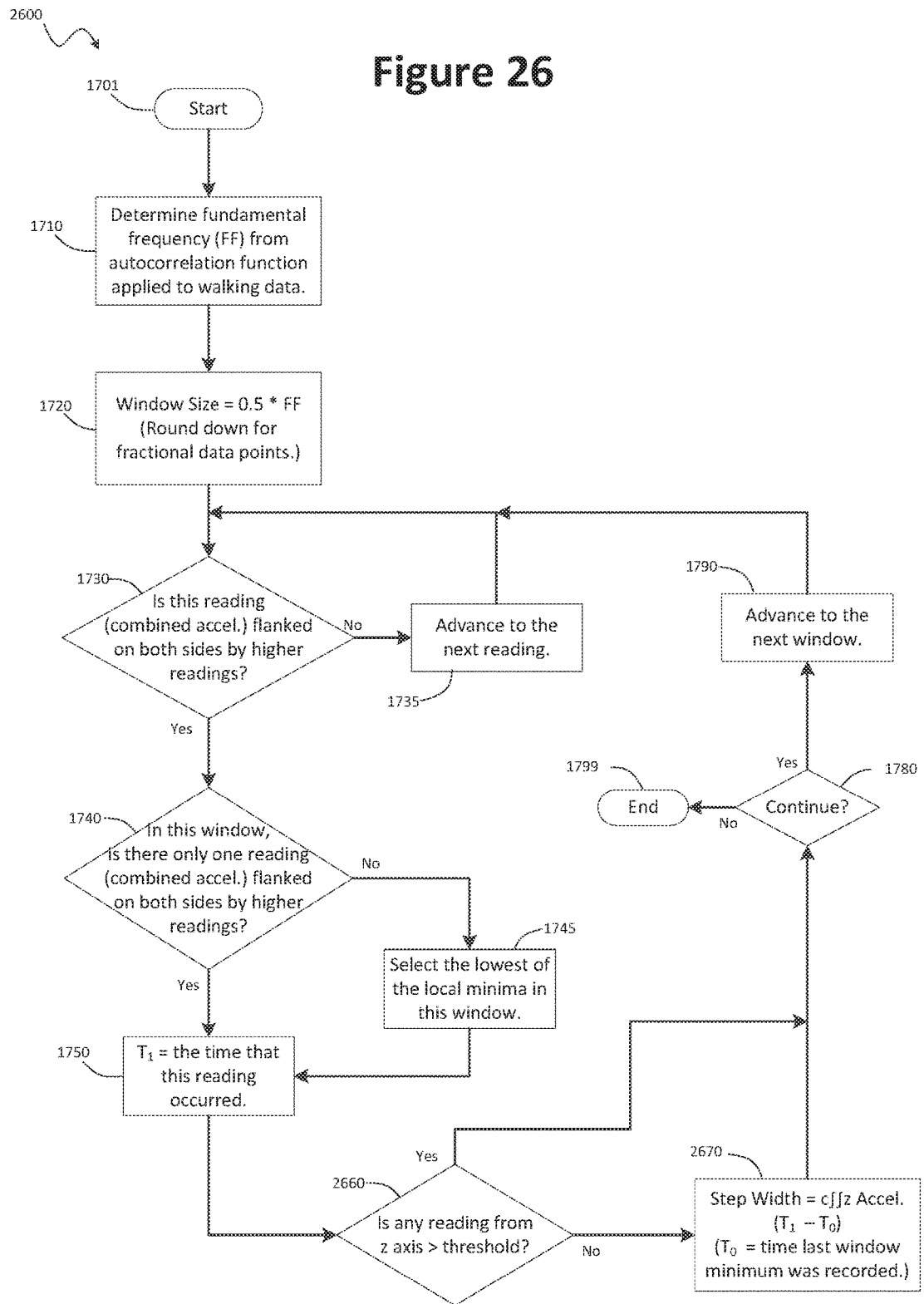
FIG. 26 presents a flow chart illustrating a method for estimating step width, according to certain embodiments of the present disclosure.

FIG. 26 presents a flow chart illustrating an embodiment of a processor-implemented method (2600) for estimating step width, according to the present disclosure. After the start (1701), the fundamental frequency from an autocorrelation function is determined (1710). Window size is set at half the fundamental frequency of the autocorrelation (1720). If half the time of the fundamental frequency includes a fraction of an accelerometer reading, the window size rounds down to the next whole number of readings (1720). Starting with the first reading in a window, the method (2600) queries whether the reading is lower than both the immediately previous reading and the immediately following reading (1730). If not, analysis proceeds to the next reading (1735). If the reading is a local minimum (flanked by greater readings), the method then queries whether the reading is the only local minimum in its window (1740). If so, the single local minimum is selected. If there are one or more other local minima in the window, the lowest of the local minima is selected (1745). The time of the selected local minimum ($T_1$) is then accessed (1750). The method (2600) then queries whether any reading from the z axis of the accelerometer exceeds a threshold (2660). If so, analysis proceeds to the next window (1790). If not, step width is estimated as a constant (c) multiplied by the double integral of acceleration on the z axis from time $T_0$ to time $T_1$ (2670). $T_0$ is the time at which the immediately previous window minimum (lowest minimum in the window) occurred. The method (2600) then queries whether to continue (1780). If so, analysis proceeds to the next window (1790). If not, the method (2600) ends (1799).

Gait Symmetry

In a healthy gait, the steps of one foot tend to be similar to those of the other. Differences between the left foot and right foot with respect to parameters such as those discussed above may indicate a problem manifesting itself in the individual's gait. Some device embodiments may compare gait metrics of the left leg to those of the right leg to assess gait symmetry. Except for embodiments that assess gait symmetry of individual steps, embodiments may use averages or other measures of central tendency for gait parameters of each foot. Embodiments may compare gait metrics of the left leg to those of the right leg over a variety of time periods depending on the particular application of the gait symmetry measurement. For example, some embodiments may assess gait symmetry based on averages of the last minute. Some embodiments may assess gait symmetry from the beginning of an episode of walking. Embodiments need not ascertain which metrics are attributable to the left leg and which are attributable to the right leg. An embodiments may assess gait symmetry if it can distinguish the activity attributable to one leg from activity attributable to the other, even without determining which leg is the left or right.

Some embodiments may assess gait in real time and provide the user feedback regarding his or her gait symmetry. Some embodiments may provide automated gait coaching. For example, a system embodiment may advise the user to take longer steps with the left leg.

Gait Variability

Variation among steps of one leg and/or variation among strides may also be indicators of gait health, with higher variation indicating potential problems manifesting in gait. However, high variation of a gait parameter does not necessarily indicate a problem. For example, walking on uneven terrain may cause an individual with an otherwise healthy gait to have high variability among steps or strides. Gait variation may refer to the variation of any gait parameter and variation may be quantified using a variety of measures such as variance, standard deviation, and average deviation.

Some embodiments may assess gait in real time and provide the user feedback regarding his or her gait symmetry. Some embodiments may provide automated gait coaching. For example, a system embodiment may provide an audible and/or visible cadence beat and advise the user to take steps on the beat, thus encouraging more regular step duration.

The above description is neither exclusive nor exhaustive and is intended neither to describe all possible embodiments (also called "examples") nor to limit the scope of the claims. Claimed embodiments may include elements in addition to those in the described embodiments and, in some cases, may contain only a subset of the elements described in a particular embodiment. Embodiments may contain any combination of elements in the described embodiments in addition to elements not expressly described. As used herein, the articles "a" and "an" may include one or more than one of the noun modified by either without respect to other uses of phrases such as "one or more" or "at least one." The word "or" is used inclusively unless specified otherwise. Terms such as "first," "second," "third" and so forth are used as labels to distinguish elements and do not indicate sequential order unless otherwise indicated. In addition to the embodiments described above, embodiments of the invention include any that would fall within the scope of the Claims, below.

As used herein, functions of numbers include, but are not limited to, the number itself. For example, the function of a number could simply subtract zero from it or multiply it by one. Functions of numbers may, for example, result in outputs that vary insignificantly from function inputs. Functions may alter values in ways that preserve the fundamental relationship among values for example, by changes in scale, inverting positive to negative numbers, or altering thresholds to accommodate changes to scale or number sign. Whether expressly stated or not, the methods described herein include functions of the mathematical components involved in the method that would not alter the potential uses of the method.

The above description of the invention is neither exclusive nor exhaustive and is intended neither to describe all possible embodiments (also called "examples") of the invention nor to limit the scope of the invention. Embodiments of the invention may include elements in addition to those in the described embodiments and, in some cases, may contain only a subset of the elements described in a particular embodiment. Embodiments may contain any combination of elements in the described embodiments in addition to elements not expressly described. As used herein, the articles "a" and "an" may include one or more than one of the noun modified by either without respect to other uses of phrases such as "one or more" or "at least one." The word "or" is used inclusively unless specified otherwise. Terms such as "first," "second," "third" and so forth are used as labels to distinguish elements and do not indicate sequential order unless specified otherwise. In addition to the embodiments described above, embodiments of the invention include any that would fall within the scope of the Claims, below. The Abstract section is provided by way of example and summary but not limitation of the invention's scope.

What is claimed is:

1. A system comprising:
   an accelerometer;
   a processor communicatively coupled to the accelerometer; and
   a non-transitory computer readable medium communicatively coupled to the processor, the non-transitory computer readable medium storing instructions controlling the processor to:
   receive readings from the accelerometer;
   determine a subset of the readings from the accelerometer to store on the non-transitory computer-readable medium based on instructions controlling the processor to:
      group readings of the accelerometer into data windows, each of the data windows corresponding to a window time period, the readings of each of the data windows generated during the respective window time period, each window time period corresponding to a different time period;
      count a number of data windows overlapping with a first time period and comprising a reading exceeding a count threshold;
      determine an activity ratio, a numerator of the activity ratio comprising the number of counted data windows overlapping with the first time period and a denominator of the activity ratio comprising a count of each of the data windows overlapping with the first time period; and
      if the activity ratio exceeds an activity threshold:
         generate the subset of the readings using the readings generated during the first time period; and
         store the subset of the readings on the non-transitory computer readable medium.

2. The system of claim 1 in which the window time period has a duration greater than or equal to one quarter (0.25) second and less than or equal to one and a half (1.5) seconds.

3. The system of claim 1 in which the count threshold is greater than or equal to 0.2 g and less than or equal to 0.8 g.

4. The system of claim 1, wherein the first time period overlaps with a critical time period, and wherein the critical time period is greater than or equal to 10 seconds and less than or equal to five minutes.

5. The system of claim 1 in which the activity threshold is greater than or equal to 0.2 and less than or equal to 1.

6. The system of claim 4 in which a first window time period overlapping with the critical time period overlaps a second window time period occurring during the critical time period.

7. The system of claim 1 in which the processor analyzes the readings generated during the first time period to determine one or more gait parameters.

8. The system of claim 7 in which the one or more gait parameters comprise at least one of: step duration, stride duration, step length, stride length, step width, stride width, lateral sway, single limb support time, or double limb support time.

9. A system comprising:
an accelerometer;
a processor communicatively coupled to the accelerometer; and
a non-transitory computer readable medium communicatively coupled to the processor, the non-transitory computer readable medium storing instructions controlling the processor to:
receive readings from the accelerometer;
determine a subset of the readings from the accelerometer to store on the non-transitory computer-readable medium based on instructions controlling the processor to:
group readings of the accelerometer into data windows, each of the data windows corresponding to a window time period, the readings of each of the data windows generated during the respective window time period;
determine a window value for each of the data windows overlapping with a first time period, the window value comprising a measure of central tendency of the readings of the each of the data windows;
identify one or more local maxima in the window values of windows overlapping with the first time period, each of the one or more local maxima called a peak;
count a number of peaks exceeding a count threshold and occurring during the first time period, each of the peaks exceeding the count threshold called a counted peak;
determine an activity ratio, a numerator of the activity ratio comprising a number of counted peaks occurring during the first time period and a denominator of the activity ratio comprising a number of all peaks occurring during the first time period; and
generate the subset of the readings using the readings generated during the first time period; and
store the subset of the readings on the non-transitory computer readable medium if the activity ratio exceeds an activity threshold.

10. The system of claim 9 in which the window time period has a duration greater than or equal to one quarter (0.25) second and less than or equal to one and a half (1.5) seconds.

11. The system of claim 9 in which the count threshold is greater than or equal to 0.2 g and less than or equal to 0.8 g.

12. The system of claim 9, wherein the first time period overlaps with a critical time period, and wherein the critical time period is greater than or equal to 10 seconds and less than or equal to five minutes.

13. The system of claim 9 in which the activity threshold is greater than or equal to 0.2 and less than or equal to 1.

14. The system of claim 12 in which a first window time period overlapping with the critical time period overlaps a second window time period occurring during the critical time period.

15. The system of claim 9 in which the processor analyzes the readings generated during the first time period to determine one or more gait parameters.

16. The system of claim 15 in which the one or more gait parameters comprise at least one of: step duration, stride duration, step length, stride length, step width, stride width, lateral sway, single limb support time, or double limb support time.

17. A processor-implemented method for selecting readings of an accelerometer to store on a non-transitory computer-readable medium, the method comprising:
receiving readings from the accelerometer;
determining a subset of the readings from the accelerometer to store on a non-transitory computer-readable medium comprising:
grouping readings into data windows, each of the data windows corresponding to a window time period, the readings of each of the data windows generated during the respective window time period;
determining a window value for each of the data windows overlapping with a first time period, the window value comprising a measure of central tendency of the readings of the each of the data windows;
identifying one or more local maxima in the window values of windows overlapping with the first time period, each of the one or more local maxima called a peak;
counting a number of peaks exceeding a count threshold and occurring during the first time period, each of the peaks exceeding the count threshold called a counted peak;
determining an activity ratio, a numerator of the activity ratio comprising the number of counted peaks occurring during the first time period and a denominator of the activity ratio comprising a count of each peak occurring during the first time period; and
generating the subset of the readings using the readings generated during the first time period; and
storing the subset of the readings on the non-transitory computer readable medium if the activity ratio exceeds an activity threshold.

18. The method of claim 17 in which the measure of central tendency is a weighted average.

19. The method of claim 17 comprising analyzing the readings generated during the first time period to determine one or more gait parameters.

20. A method comprising:
receiving accelerometer readings from an accelerometer;
iteratively, over a first duration, determining subsets of accelerometer readings to store in a non-transitory computer-readable medium comprising and storing the determined subsets comprising:
grouping accelerometer readings into data windows, each of the data windows corresponding to a window time period, the readings of each of the data windows generated during the respective window time period, each window time period corresponding to a different time period;
defining successive time periods having at least one data window;
for each time period:
counting numbers of data windows of the respective time period having accelerometer readings exceeding a count threshold;
determining an activity ratio for the respective time period, a numerator of the activity ratio comprising the number of counted data windows within the respective time period and a denominator of the activity ratio comprising a count of each of the data windows within the respective time period;
if the activity ratio exceeds an activity threshold:

generating a subset of accelerometer readings for the respective time period comprising accelerometer readings within the data windows of the respective time period;

storing the subset of accelerometer readings to the non-transitory computer-readable medium;

otherwise, advancing to the next time period.

21. The method of claim 20 further comprising, for each time period, determining one or more gait parameters based on the accelerometer readings during the respective time period.

22. The system of claim 1, wherein the non-transitory computer readable medium storing instructions further controlling the processor to:

determine one or more gait parameters based on the subset of the readings;

receive second readings from the accelerometer;

determine a second subset of the second readings from the accelerometer to store on the non-transitory computer-readable medium based on instructions controlling the processor to:

group seconds readings of the accelerometer into second data windows, each of the second data windows corresponding to a window time period, the readings of each of the second data windows generated during the respective window time period, each window time period corresponding to a different time period;

count a number of second data windows overlapping with a second time period and comprising a reading exceeding a count threshold;

determine a second activity ratio, a numerator of the second activity ratio comprising the number of counted second data windows overlapping with the second time period and a denominator of the second activity ratio comprising a count of each of the second data windows overlapping with the second time period; and if the second activity ratio exceeds the activity threshold:

generate the second subset of the second readings using the second readings generated during the second time period; and store the second subset of the second readings on the non-transitory computer readable medium; and determine one or more second gait parameters based on the second subset of the second readings; and determine a characteristic of a movement of a person based on the first and second gait parameters.

* * * * *